(12) United States Patent
Gordon

(10) Patent No.: US 6,602,849 B1
(45) Date of Patent: Aug. 5, 2003

(54) CYCLIC SOMATOSTATIN ANALOGS

(75) Inventor: Thomas D. Gordon, Medway, MA (US)

(73) Assignee: Societe de Conseils de Recherche et d'Applications Scientifiques, S.A.S., Paris (FR)

( * ) Notice: Subject to any disclaimer, the term of this patent is extended or adjusted under 35 U.S.C. 154(b) by 0 days.

(21) Appl. No.: 09/719,784

(22) PCT Filed: Jun. 11, 1999

(86) PCT No.: PCT/US99/13304

§ 371 (c)(1),
(2), (4) Date: Feb. 14, 2001

(87) PCT Pub. No.: WO99/65942

PCT Pub. Date: Dec. 23, 1999

Related U.S. Application Data

(60) Provisional application No. 60/089,503, filed on Jun. 16, 1998.

(51) Int. Cl.[7] ........................ A61K 38/08; A61K 38/12; A61K 38/31; C07K 5/12; C07K 14/655
(52) U.S. Cl. ................ 514/2; 514/11; 514/17; 514/393; 514/399; 514/400; 530/300; 530/311; 530/317; 530/332; 548/302.7; 548/340.1
(58) Field of Search ................... 514/2, 11, 14, 514/17, 19, 393, 394, 399, 400; 530/300, 311, 317, 332; 548/302.7, 309.7, 338.1, 340.1

(56) References Cited

FOREIGN PATENT DOCUMENTS

| WO | WO 97/30053 | 8/1997 |
|---|---|---|
| WO | WO 98/04583 | 2/1998 |

OTHER PUBLICATIONS

Abell et al. Synthesis of 1,2–Disubstituted Pyrolles . . . Tet. Lett. 1992, vol. 33, No. 39, pp. 5831–5832.*
Gordon et al. Synthetic Approaches to the Azole Peptide Mimetics. 1993, Tet. Lett., vol. 34, No. 12, pp. 1901–1904.*
Beusen et al. Conformational Mimicry: Synthesis and Solution . . . Biopolymers. 1995, vol. 36, pp. 181–200.*
Ankersen et al. Discovery of a Novel Non–Peptide Somatostatin Agonist with SST4 Selectivity. J. Am. Chem. Soc. Feb. 4, 1998, vol. 120, No. 7, pp. 1368–1373.*
Hepato–gastroenterology. May–Jun. 1998, vol. 45, pp. 761–764.*
Arzneim–Forschung Drug Research. 1997, vol. 47, p. 475.*
Shimon L. et al. "Somatostatin Receptor Subtype Specificity in Human Fetal Pituitary Cultures"; Journal of Clinical Investigation, vol. 99, No.: 4,; (1997), pp. 789–798.
Gilon, Chaim E.A.; "A backbone–cyclic, receptor 5–selective somatostatin analogue: synthesis, bioactivity and NMR conformational analysis"; Journal of Medicinal Chemistry, vol. 41, No. 5,; pp. 919–929; (1998).

* cited by examiner

*Primary Examiner*—Jeffrey E. Russel
(74) *Attorney, Agent, or Firm*—Fish & Richardson; Brian R. Morrill; Alan F. Feeney

(57) ABSTRACT

The present invention is directed to cyclic derivatives containing an imidazole cis amide bond mimetic which bind selectively to somatostatin receptor subtypes and the use thereof in treating conditions which can be treated by eliciting an agonist or antagonist effect from the somatostatin subtype receptors. This invention is also directed to methods for making the compounds of the instant invention.

25 Claims, No Drawings

CYCLIC SOMATOSTATIN ANALOGS

CROSS REFERENCE TO RELATED APPLICATIONS

This application is a 371 of PCT/US99/13304, with an international filing date Jun. 11, 1999, which claims the benefit of U.S. Provisional Patent Application No. 60/089,503, filed Jun. 16, 1998.

BACKGROUND OF THE INVENTION

The present invention is directed to cyclic derivatives containing an imidazole cis amide bond mimetic which bind selectively to somatostatin receptor subtypes. This invention is also directed to methods for making the compounds of the instant invention.

Somatostatin (SRIF) is a cyclic tetradecapeptide hormone containing a disulfide bridge between position 3 and position 14 and has the properties of inhibiting the release of growth hormone (GH) and thyroid-stimulating hormone (TSH), inhibiting the release of insulin and glucagon, and reducing gastric secretion. Metabolism of somatostatin by aminopeptidases and carboxypeptidases leads to a short duration of action.

Somatostatin binds to five distinct receptor (SSTR) subtypes with relatively high affinity for each subtype. The smaller, more rigid analogs of the present invention exhibit high selectivity for several of the receptor subtypes. Binding to the different types of somatostatin subtypes have been associated with the treatment of the following conditions and/or diseases. Activation of types 2 and 5 have been associated with growth hormone suppression and more particularly GH secreting adenomas (Acromegaly) and TSH secreting adenomas. Activation of type 2 but not type 5 has been associated with treating prolactin secreting adenomas. Other indications associated with activation of the somatostatin subtypes are restenosis, inhibition of insulin and/or glucagon and more particularly diabetes mellitus, hyperlipidemia, insulin insensitivity, Syndrome X, angiopathy, proliferative retinopathy, dawn phenomenon and Nephropathy; inhibition of gastric acid secretion and more particularly peptic ulcers, enterocutaneous and pancreaticocutanieous fistula, irritable bowel syndrome, Dumping syndrome, watery diarrhea syndrome, AIDS related diarrhea, chemotherapy-induced diarrhea, acute or chronic pancreatitis and gastrointestinal hormone secreting tumors; treatment of cancer such as hepatoma; inhibition of angiogenesis, treatment of inflammatory disorders such as arthritis; chronic allograft rejection; angioplasty; preventing graft vessel and gastrointestinal bleeding. Somatostatin agonists can also be used for decreasing body weight in a patient.

Somatostatin agonists have also been disclosed to be useful for inhibiting the proliferation of *helicobacter pylori*.

SUMMARY OF THE INVENTION

In one aspect, the present invention provides a compound of the formula (I),

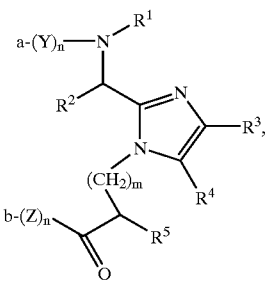

or a pharmaceutically acceptable salt thereof, wherein,

Y and Z for each occurrence are each independently a D- or L-natural or unnatural α-amino acid;

n for each occurrence is independently 0 to 50, provided that both n cannot be 0 at the same time;

m is 0 or an integer from 1 to 10;

a is H or $R^1$;

b is OH, —$OR^1$ or —$NR^9R^9$;

or a is taken together with b to form an amide bond;

$R^1$ is independently H, ($C_1$–$C_4$)alkyl or aryl-($C_1$–$C_4$)alkyl;

$R^2$ is H or an optionally substituted moiety selected from the group consisting of ($C_1$–$C_4$)alkyl, phenyl, phenyl-($C_1$–$C_4$)alkyl and heterocyclyl-($C_1$–$C_4$)alkyl, where the optionally substituted moiety is optionally substituted by one or more substituents each independently selected from the group consisting of ($C_1$–$C_4$)alkyl, ($C_3$–$C_8$)cycloalkyl, —O—$R^6$, —$S(O)_q$—$R^7$, —$N(R^9R^9)$, —NHCO—$R^6$, —$NHSO_2R^9$, —$CO_2R^9$, —$CONR^9R^9$ and —$SO_2NR^9R^9$, where q is 0, 1, 2 or 3;

$R^3$ and $R^4$ are each independently H, halo or an optionally substituted moiety selected from the group consisting of ($C_1$–$C_4$)alkyl, ($C_3$–$C_8$)cycloalkyl, aryl and aryl-($C_1$–$C_4$)alkyl; where the optionally substituted moiety is optionally substituted by one or more substituents selected from the group consisting of OH, ($C_1$–$C_4$) alkyl, ($C_1$–$C_4$)alkoxy, aryloxy, aryl-($C_1$–$C_4$)alkoxy, —$NR^9R^9$, COOH, —$CONR^9R^9$ and halo;

or $R^3$ and $R^4$ are taken together with the carbons to which they are attached to form optionally substituted aryl, where the aryl is optionally substituted by one or more substituents each independently selected from the group consisting of OH, ($C_1$–$C_4$)alkyl, ($C_1$–$C_4$)alkoxy, aryloxy, aryl-($C_1$–$C_4$)alkoxy, —$NR^9R^9$, $COOR^5$, —$CONR^9R^9$ and halo;

$R^5$ for each occurrence is independently H, or an optionally substituted moiety selected from the group consisting of ($C_1$–$C_4$)alkyl and aryl-($C_1$–$C_4$)alkyl, where the optionally substituted moiety is optionally substituted by one or more substituents each independently selected from the group consisting of ($C_1$–$C_4$)alkyl, OH, ($C_1$–$C_4$)alkoxy, aryloxy, $NO_2$, aryl-($C_1$–$C_4$,)alkoxy, —$NR^9R^9$, COOH, —$CONR^9R^9$ and halo;

$R^6$ for each occurrence is independently selected from the group consisting of H, ($C_1$–$C_4$)alkyl, ($C_1$–$C_4$)alkoxy, aryl-($C_1$–$C_4$)alkyl and aryl-($C_1$–$C_4$)alkoxy;

$R^7$ is H when q is 3 or, $R^7$ for each occurrence is independently selected from the group consisting of ($C_1$–$C_4$)alkyl, aryl and aryl-($C_1$–$C_4$)alkyl when q is 0, 1 or 2; and R$^9$ for each occurrence is independently selected from the group consisting of H, NO$_2$, (C$_1$–C$_4$)alkyl, aryl and aryl-(C$_1$–C$_4$)alkyl.

A preferred compound of formula (I) is the compound H-Trp-D-Trp-Lys-Abu-Phe Ψ (4-(3-methoxyphenyl) imidazole)-Gly-OH.

In another aspect, the present invention provides a compound of the formula (II),

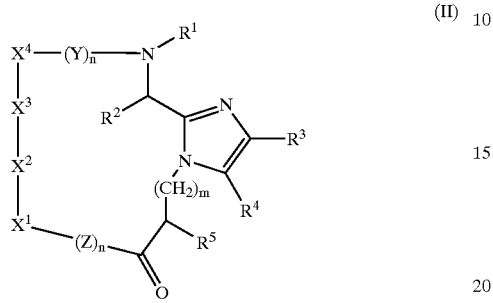

or a pharmaceutically acceptable salt thereof, wherein,

Y and Z for each occurrence are each independently a D- or L-natural or unnatural α-amino acid;

m is 0 or an integer from 1 to 10;

n for each occurrence is independently 0 to 6;

R$^1$ for each occurrence is independently H, (C$_1$–C$_4$)alkyl or aryl-(C$_1$–C$_4$)alkyl;

R$^2$ is H or an optionally substituted moiety selected from the group consisting of (C$_1$–C$_4$)alkyl, phenyl, phenyl-(C$_1$–C$_4$)alkyl and heterocyclyl-(C$_1$–C$_4$)alkyl, where the optionally substituted moiety is optionally substituted by one or more substituents each independently selected from the group consisting of (C$_1$–C$_4$)alkyl, cycloalkyl, —O—R$^6$, —S(O)$_q$—R$^7$, —N(R$^9$R$^9$), —NHCO—R$^8$, —NHSO$_2$R$^9$, —CO$_2$R$^9$, —CONR$^9$R$^9$ and —SO$_2$NR$^9$R$^9$, where q is b, 1, 2 or 3;

R$^3$ and R$^4$ are each independently H, halo or an optionally substituted moiety selected from the group consisting of (C$_1$–C$_4$)alkyl, cycloalkyl, aryl and aryl-(C$_1$–C$_4$) alkyl; where the optionally substituted moiety is optionally substituted by one or more substituents selected from, the group consisting of OH, (C$_1$–C$_4$) alkyl, (C$_1$–C$_4$)alkoxy, aryloxy, aryl-(C$_1$–C$_4$)alkoxy, —NR$^9$R$^9$, COOH, —CONR$^9$R$^9$ and halo;

or R$^3$ and R$^4$ are taken together with the carbons to which they are attached to form optionally substituted aryl, where the aryl is optionally substituted by one or more substituents each independently selected from the group consisting of OH, (C$_1$–C$_4$)alkyl, (C$_1$–C$_4$)alkoxy, aryloxy, aryl-(C$_1$–C$_4$)alkoxy, —NR$^9$R$^9$, COOR$^5$, —CONR$^9$R$^9$ and halo;

R$^5$ for each occurrence is independently H, or an optionally substituted moiety selected from the group consisting of (C$_1$–C$_4$)alkyl and aryl-(C$_1$–C$_4$)alkyl, where the optionally substituted moiety is optionally substituted by one or more substituents each independently selected from the group consisting of (C$_1$–C$_4$)alkyl, OH, (C$_1$–C$_4$)alkoxy, aryloxy, NO$_2$, aryl-(C$_1$–C$_4$) alkoxy, —NR$^9$R$^9$, COOH, —CONR$^9$R$^9$ and halo;

R$^6$ for each occurrence is independently selected from the group consisting of H, (C$_1$–C$_4$)alkyl, (C$_1$–C$_4$) alkoxy, aryl-(C$_1$–C$_4$)alkyl and aryl-(C$_1$–C$_4$)alkoxy;

R$^7$ is H when q is 3, or R$^7$ for each occurrence is independently selected from the group consisting of (C$_1$–C$_4$)alkyl, aryl and aryl-(C$_1$–C$_4$)alkyl when q is 0, 1 or 2; and R$^9$ for each occurrence is independently selected from the group consisting of H, NO$_2$, (C$_1$–C$_4$)alkyl, aryl and aryl-(C$_1$–C$_4$)alkyl;

X$^1$ is a natural or unnatural D- or L-α-amino acid, where when X$^1$ is Phe, NaI, Trp, Tyr, PaI or His the aromatic ring thereof is optionally substituted on carbon or nitrogen by R$^6$ or when X$^1$ is Ser or Thr, the side chain oxygen is optionally substituted by one or more R$^1$;

X$^2$ is D- or L-Trp, N-methyl-D-Trp or N-methyl-L-Trp;

X$^3$ is Lys, α-N-methyl-Lys or ε-N-(C$_1$–C$_4$)alkyl-Lys or ε-N-[aryl-(C$_1$–C$_4$)alkyl]-Lys;

X$^4$ is a natural or unnatural D- or L-α-amino acid where when X$^4$ is Phe, NaI, Trp, Tyr or His, the aromatic ring thereof is optionally substituted on carbon or nitrogen by R$^8$ or when X$^4$ is Ser, Tyr or Thr, the side chain oxygen may be substituted with one or more R$^1$.

The bonds between X$^1$, X$^2$, X$^3$ and X$^4$ are amide bonds as is the bond between X$^1$ and Z, and the bond between X$^4$ and Y.

A preferred group of compounds of formula (II), designated group A, is wherein, each n is 2;

m is 0 or 1 to 5;

R$^1$ for each occurrence is independently H, methyl or aryl-(C$_1$–C$_4$)alkyl;

R$^2$ is an optionally substituted moiety selected from the group consisting phenyl-(C$_1$–C$_4$)alkyl and heterocyclyl-(C$_1$–C$_4$)alkyl, where the optionally substituted moiety is substituted by a substituent selected from the group consisting of (C$_1$–C$_4$)alkyl and —O—R$^6$; and R$^3$ and R$^4$ are each independently H, halo or an optionally substituted moiety selected from the group consisting of (C$_1$–C$_4$)alkyl and aryl; where the optionally substituted moiety is optionally substituted by a substituent selected from the group consisting of OH, (C$_1$–C$_4$) alkoxy, aryloxy and halo.

A preferred group of the.group A compounds, designated group B, is wherein

X$^1$ is Phe, NaI, Trp, Tyr, PaI or His, wherein the aromatic ring thereof is optionally substituted on carbon or nitrogen by R$^6$; and X$^4$ is Val, Abu, Ser, Thr, NaI, Trp, Tyr or His, wherein the aromatic ring of NaI, Trp, Tyr and His is optionally substituted on carbon and/or nitrogen by R$^8$ or when X$^4$ is Ser, Tyr or Thr, the side chain oxygen is optionally substituted by R$^1$.

A preferred group of the group B compounds, designated group C, is wherein

X$^1$ is Phe, Trp or Tyr wherein the aromatic ring thereof is optionally substituted on carbon or nitrogen by R$^6$;

X$^2$ is D-Trp or N-methyl-D-Trp;

X$^4$ is Val, Thr, Abu, NaI or Tyr, wherein the side chain oxygen of the hydroxy group of Thr and Tyr is optionally substituted by R$^1$;

R$^1$ for each occurrence is independently H, methyl or benzyl;

R$^2$ is an optionally substituted moiety selected from the group consisting phenylmethyl and heterocyclyl-methyl, where the optionally substituted moiety is substituted by a substituent selected from the group consisting of (C$_1$–C$_4$)alkyl and —O—R$^6$;

R³ is (C₁–C₄)alkyl or optionally substituted aryl; where the optionally substituted aryl is substituted by a substituent selected from the group consisting of OH, (C₁–C₄)alkoxy, aryloxy, and halo;

R⁴ is H; and

R⁶ for each occurrence is independently selected from the group consisting of H and aryl-(C₁–C₄)alkoxy.

A preferred group of the group C compounds, designated group D, is wherein X¹ is Phe, Trp, Tyr or Tyr(OBzl);

X⁴ is Val, Thr, Abu, NaI, or Tyr, wherein the hydroxy group of Thr and Tyr is optionally substituted benzyl;

m is 0, 2 or 4;

R² is an optionally substituted moiety selected from the group consisting of phenylmethyl and 3-indolylmethyl where the optionally substituted moiety is optionally substituted by —O—R⁶; and R³ is 1,1-dimethylethyl or optionally substituted aryl; where the optionally substituted aryl is optionally substituted by a moiety selected from the group consisting of OH, (C₁–C₄)alkoxy and halo.

A preferred group of the group D compounds, designated group E, is wherein

R² is phenylmethyl;

R³ is 1,1-dimethylethyl or optionally substituted phenyl, where the optionally substituted phenyl is optionally substituted by OH or OCH₃; and R⁶ for each occurrence is independently selected from the group consisting of H and benzylmethoxy.

A preferred group of the group, E compounds, designated group F, is cyclo[Tyr-D-Trp-Lys-Val-PheΨ(4-(3-methoxyphenyl)imidazole)-Gly], cyclo[Tyr(OBzl)-D-Trp-Lys-Val-PheΨ(4-(3-methoxyphenyl)imidazole)-Gly], cyclo[Trp-D-Trp-Lys-Val-PheΨ(4-(3-methoxyphenyl)imidazole)-Gly], cyclo[Trp-D-Trp-Lys-Val-PheΨ(4-(3-hydroxyphenyl)imidazole)-Gly], cyclo[Trp-D-Trp-Lys-Thr(OBzl)-PheΨ(4-(3-methoxyphenyl)imidazole)-Gly], cyclo[Trp-D-Trp-Lys-Thr-PheΨ(4-(3-hydroxyphenyl)imidazole)-Gly], cyclo[Trp-D-Trp-Lys-Abu-PheΨ(4-(3-methoxyphenyl)imidazole)-Gly], cyclo[Phe-D-Trp-Lys-Tyr(OBzl)-PheΨ(4-(1,1-dimethylethyl)imidazole)-Gly], cyclo[Phe-D-Trp-Lys-Val-PheΨ(4-(3-methoxyphenyl)imidazole)-Gly], cyclo[Phe-D-Trp-Lys-Tyr(OBzl)-PheΨ(4-(3-methoxyphenyl)imidazole)-Gly], cyclo[Phe-D-Trp-Lys-Tyr-PheΨ(4-(3-methoxyphenyl)imidazole)-Gly], cyclo[Phe-D-Trp-Lys-Tyr-PheΨ(4-(3-hydroxyphenyl)imidazole)-Gly], cyclo[Trp-D-Trp-Lys-Tyr(Bzl)-PheΨ(4-(3-methoxyphenyl)imidazole)-Gly], cyclo[Tyr-D-Trp-Lys-Val-PheΨ(4-(3-hydroxyphenyl)imidazole)-Gly], cyclo[Phe-D-Trp-Lys-NaI-PheΨ(4-(3-hydroxyphenyl)imidazole)-Gly], cyclo[Phe-D-Trp-Lys-NaI-PheΨ(4-(3-methoxyphenyl)imidazole)-Gly], cyclo[Trp-D-Trp-Lys-Tyr(OBzl)-PheΨ(4-(3-methoxyphenyl)imidazole)-(γ)Abu], cyclo[Trp-D-Trp-Lys-Tyr(OBzl)-PheΨ(4-(4-methoxyphenyl)imidazole)-Gly], cyclo[Trp-D-Trp-Lys-Tyr(OBzl)-PheΨ(4-(phenyl)imidazole)-Gly], cyclo[Trp-D-Trp-Lys-Tyr(OBzl)-PheΨ(4-(3-methoxyphenyl)imidazole)-(ε)Ahx] and cyclo[Trp-D-Trp-Lys-Tyr(OBzl)-PheΨ(4-(3-hydroxyphenyl)imidazole)-(γ)Abu].

A preferred group of the group F compounds, designated group G, is cyclo[Tyr-D-Trp-Lys-Val-PheΨ(4-(3-methoxyphenyl)imidazole)-Gly], cyclo[Tyr(OBzl)-D-Trp-Lys-Val-PheΨ(4-(3-methoxyphenyl)imidazole)-Gly], cyclo[Trp-D-Trp-Lys-Val-PheΨ(4-(3-methoxyphenyl)imidazole)-Gly], cyclo[Trp-D-Trp-Lys-Val-PheΨ(4-(3-hydroxyphenyl)imidazole)-Gly], cyclo[Trp-D-Trp-Lys-Thr(OBzl)-PheΨ(4-(3-methoxyphenyl)imidazole)-Gly], cyclo[Trp-D-Trp-Lys-Thr-PheΨ(4-(3-hydroxyphenyl)imidazole)-Gly], cyclo[Trp-D-Trp-Lys-Abu-PheΨ(4-(3-methoxyphenyl)imidazole)-Gly], cyclo[Phe-D-Trp-Lys-Tyr(OBzl)-PheΨ(4-(1,1-dimethylethyl)imidazole)-Gly], cyclo[Phe-D-Trp-Lys-Val-PheΨ(4-(3-methoxyphenyl)imidazole)-Gly], cyclo[Phe-D-Trp-Lys-Tyr-PheΨ(4-(3-hydroxyphenyl)imidazole)-Gly] and cyclo[Tyr-D-Trp-Lys-Val-PheΨ(4-(3-hydroxyphenyl)imidazole)-Gly].

A preferred group of the group G compounds, designated group H, is cyclo[Tyr-D-Trp-Lys-Val-PheΨ(4-(3-methoxyphenyl)imidazole)-Gly], cyclo[Trp-D-Trp-Lys-Val-PheΨ(4-(3-methoxyphenyl)imidazole)-Gly], cyclo[Trp-D-Trp-Lys-Val-PheΨ(4-(3-hydroxyphenyl)imidazole)-Gly], cyclo[Trp-D-Trp-Lys-Thr-PheΨ(4-(3-hydroxyphenyl)imidazole)-Gly], cyclo[Trp-D-Trp-Lys-Abu-PheΨ(4-(3-methoxyphenyl)imidazole)-Gly], cyclo[Phe-D-Trp-Lys-Val-PheΨ(4-(3-methoxyphenyl)imidazole)-Gly] or cyclo[Tyr-D-Trp-Lys-Val-PheΨ(4-(3-hydroxyphenyl)imidazole)-Gly].

A preferred group of the group H compounds, designated group I, is cyclo[Tyr-D-Trp-Lys-Val-PheΨ(4-(3-methoxyphenyl)imidazole)-Gly], cyclo[Trp-D-Trp-Lys-Val-PheΨ(4-(3-hydroxyphenyl)imidazole)-Gly], cyclo[Trp-D-Trp-Lys-Thr-PheΨ(4-(3-hydroxyphenyl)imidazole)-Gly] and cyclo[Tyr-D-Trp-Lys-Val-PheΨ(4-(3-hydroxyphenyl)imidazole)-Gly].

Another preferred group of the group F compounds, designated group J, cyclo[Tyr-D-Trp-Lys-Val-PheΨ(4-(3-methoxyphenyl)
  imidazole)-Gly],
cyclo[Trp-D-Trp-Lys-Val-PheΨ(4-(3-methoxyphenyl)
  imidazole)-Gly],
cyclo[Trp-D-Trp-Lys-Val-PheΨ(4-(3-hydroxyphenyl)
  imidazole)-Gly],
cyclo[Trp-D-Trp-Lys-Thr(OBzl)-PheΨ(4-(3-
  methoxyphenyl)imidazole)-Gly],
cyclo[Trp-D-Trp-Lys-Thr-PheΨ(4-(3-hydroxyphenyl)
  imidazole)-Gly],
cyclo[Trp-D-Trp-Lys-Abu-PheΨ(4-(3-methoxyphenyl)
  imidazole)-Gly],
cyclo[Phe-D-Trp-Lys-Tyr(OBzl)-PheΨ(4-(1,1-
  dimethylethyl)imidazole)-Gly],
cyclo[Phe-D-Trp-Lys-Tyr(OBzl)-PheΨ(4-(3-
  methoxyphenyl)imidazole)-Gly],
cyclo[Phe-D-Trp-Lys-Tyr-PheΨ(4-(3-hydroxyphenyl)
  imidazole)-Gly],
cyclo[Trp-D-Trp-Lys-Tyr(OBzl)-PheΨ(4-(3-
  methoxyphenyl)imidazole)-Gly],
cyclo[Tyr-D-Trp-Lys-Val-PheΨ(4-(3-hydroxyphenyl)
  imidazole)-Gly],
cyclo[Phe-D-Trp-Lys-NaI-PheΨ(4-(3-hydroxyphenyl)
  imidazole)-Gly],
cyclo[Phe-D-Trp-Lys-NaI-PheΨ(4-(3-methoxyphenyl)
  imidazole)-Gly],
cyclo[Trp-D-Trp-Lys-Tyr(OBzl)-PheΨ(4-(3-
  methoxyphenyl)imidazole)-(γ)Abu],
cyclo[Trp-D-Trp-Lys-Tyr(OBzl)-PheΨ(4-(4-
  methoxyphenyl)imidazole)-Gly],
cyclo[Trp-D-Trp-Lys-Tyr(OBzl)-PheΨ(4-(phenyl)
  imidazole)-Gly],
cyclo[Trp-D-Trp-Lys-Tyr(OBzl)-PheΨ(4-(3-
  methoxyphenyl)imidazole)-(ε)Ahx] and
cyclo[Trp-D-Trp-Lys-Tyr(OBzl)-PheΨ(4-(3-
  hydroxyphenyl)imidazole)-(γ)Abu].
A preferred group of the group.J compounds, designated
group K, is
  cyclo[Trp-D-Trp-Lys-Thr-PheΨ(4-(3-hydroxyphenyl)
    imidazole)-Gly],
  cyclo[Trp-D-Trp-Lys-Tyr(OBzl)-PheΨ(4-(3-
    methoxyphenyl)imidazole)-Gly],
  cyclo[Phe-D-Trp-Lys-NaI-PheΨ(4-(3-hydroxyphenyl)
    imidazole)-Gly],
  cyclo[Trp-D-Trp-Lys-Tyr(OBzl)-PheΨ(4-(3-
    methoxyphenyl)imidazole)-(γ)Abu],
  cyclo[Trp-D-Trp-Lys-Tyr(OBzl)-PheΨ(4-(4-
    methoxyphenyl)imidazole)-Gly] or
  cyclo[Trp-D-Trp-Lys-Tyr(OBzl)-PheΨ(4-(phenyl)
    imidazole)-Gly].
A preferred group of the group K compounds, designated
group L, is
  cyclo[Trp-D-Trp-Lys-Tyr(OBzl)-PheΨ(4-(3-
    methoxyphenyl)imidazole)-Gly],
  cyclo[Trp-D-Trp-Lys-Tyr(OBzl)-PheΨ(4-(3-
    methoxyphenyl)imidazole)-(γ)Abu],
  cyclo[Trp-D-Trp-Lys-Tyr(OBzl)-PheΨ(4-(4-
    methoxyphenyl)imidazole)-Gly] and
  cyclo[Trp-D-Trp-Lys-Tyr(OBzl)-PheΨ(4-(phenyl)
    imidazole)-Gly].
In another aspect, the present invention provides a pharmaceutical composition comprising an effective amount of a compound of formula (I) or formula (II) or a pharmaceutically acceptable salt thereof and a pharmaceutically acceptable carrier.

In still another aspect, the present invention provides a method of eliciting a somatostatin receptor agonist effect in a mammal in need thereof, which comprises administering to said mammal an effective amount of a compound of formula (I) or formula (II) or a pharmaceutically acceptable salt thereof.

In yet another aspect, the present invention provides a method of eliciting a somatostatin receptor antagonist effect in a mammal in need thereof, which comprises administering to said mammal an effective amount of a compound according of formula (I) or formula (II) or a pharmaceutically acceptable salt thereof.

In another aspect, the present invention provides a method of treating prolactin secreting adenomas, restenosis, diabetes mellitus, hyperlipidemia, insulin insensitivity, Syndrome X, angiopathy, proliferative retinopathy, dawn phenomenon, Nephropathy, gastric acid secretion, peptic ulcers, enterocutaneous and pancreaticocutaneous fistula, irritable bowel syndrome, Dumping syndrome, watery diarrhea syndrome, AIDS related diarrhea, chemotherapy-induced diarrhea, acute or chronic pancreatitis, gastrointestinal hormone secreting tumors, cancer, hepatoma, angiogenesis, inflammatory disorders, arthritis, chronic allograft rejection, angioplasty, graft vessel bleeding or gastrointestinal bleeding, in a mammal in need thereof, which comprises administering to said mammal a compound of formula (I) or formula (II) or a pharmaceutically acceptable salt thereof.

In another aspect, this invention provides a method of inhibiting the proliferation of *helicobacter pylori* in a mammal in need thereof, which comprises administering to said mammal a compound of formula (I) or formula (II) or a pharmaceutically acceptable salt thereof.

In another aspect, this invention provides a process for preparing a compound of the formula

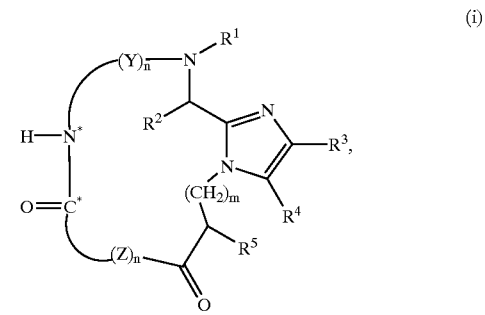

(i)

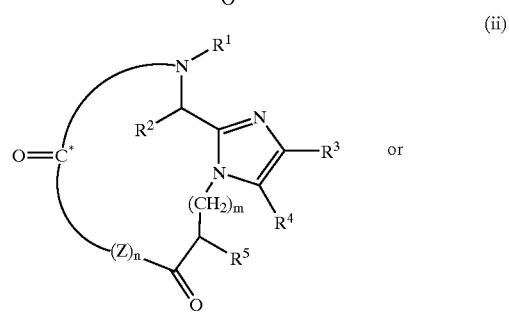

(ii)

or

-continued

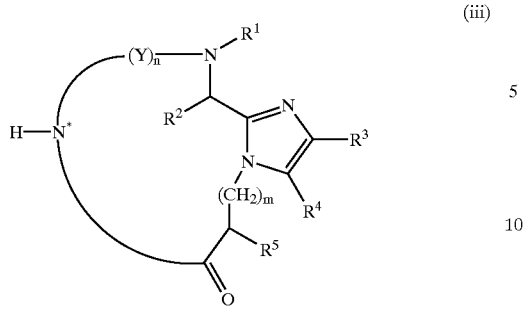
(iii)

which-comprises deprotecting a compound of the formula

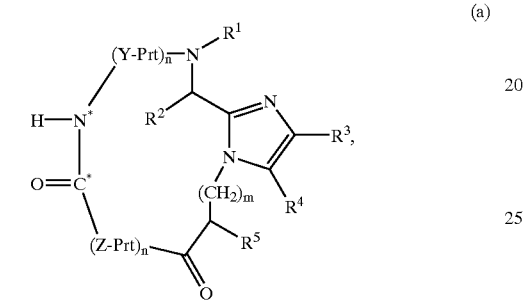
(a)

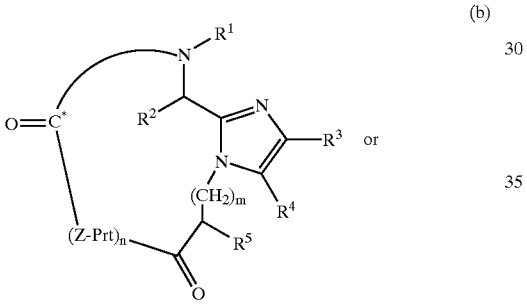
(b)

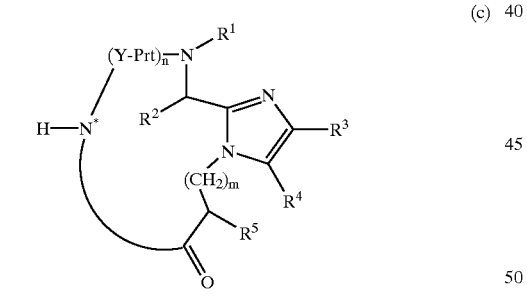
(c)

by cleaving the Prt group;
wherein,
 Prt is an amino acid side chain protecting group;
 Y and Z are each independently a D- or L-natural or unnatural α-amino acid optionally having a protected side chain, where the H—N* is the amino group of the N-terminal amino acid defined by Y and O=C* is the carboxyl group of the C-terminal amino acid defined by Z;
 n for each occurrence is independently 1 to 50;
and all other variables are as defined for formula (I) shown hereinabove.

In another aspect, the present invention provides, a process for preparing a compound of the formula

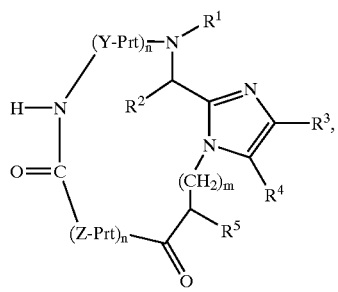
(a)

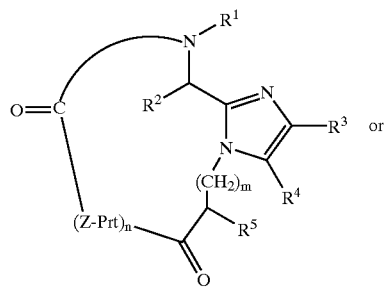
(b)

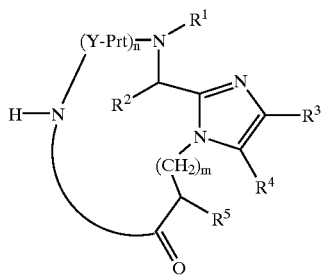
(c)

which comprises:

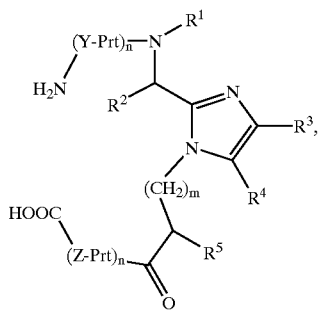
(a′)

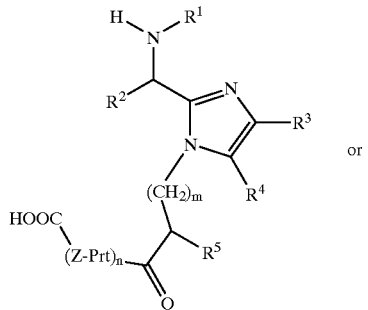
(b′)

-continued

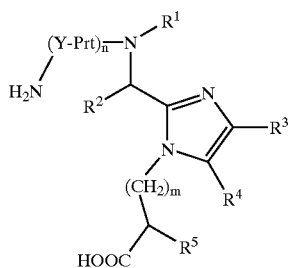

(c')

for a compound of formula (a), forming an amide bond between the terminal amino group of the last amino acid defined by Y and the terminal carboxyl group of the last amino acid defined by Z by reacting a compound of the formula (a') with a peptide coupling reagent and an additive; or for a compound of formula (b), forming an amide bond between the terminal amino group, and the terminal carboxyl group of the last amino acid defined by Z by reacting a compound of the formula (b') with a peptide coupling reagent and an additive; or for a compound of formula (c), forming an amide bond between the terminal amino group of the last amino acid defined by Y and the terminal carboxyl group by reacting a compound of the formula (c') with a peptide coupling reagent and an additive;

wherein, Prt is an amino acid side chain protecting group;

Y and Z are each independently a D- or L-natural or unnatural α-amino acid optionally having a protected side chain, where the H—N* is the amino group of the N-terminal amino acid defined by Y and O=C* is the carboxyl group of the C-terminal amino acid defined by Z;

n for each occurrence is independently 1 to 50;

and all other variables are as defined for formula (I) shown hereinabove.

In still another aspect, the present invention provides a process for preparing a compound of the formula

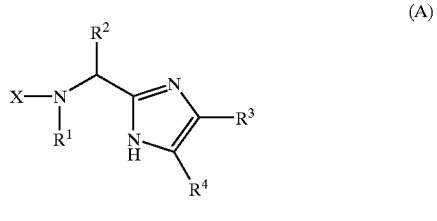

(A)

which comprises reacting a compound of the formula

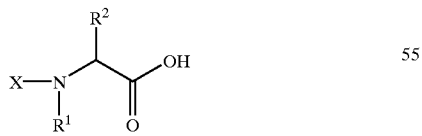

with an α-halo ketone of the formula X'—CH(R³)CO(R⁴) in the presence of a base and a polar aprotic solvent until the reaction is substantially complete; evaporating the polar aprotic solvent to yield a solid; dissolving the solid in an aprotic organic solvent and an excess amount of aqueous $NH_4OAc$ to form a solution; and refluxing the solution and concurrently removing that polar layer to yield a compound of formula (A); wherein X is an amine protecting group;

X' is halo;

and all other variables are as defined for formula (I) shown hereinabove.

In yet another aspect, this invention provides a process for preparing a compound of the formula (I),

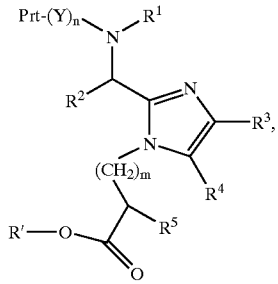

(I)

which comprises coupling a compound of the formula (B),

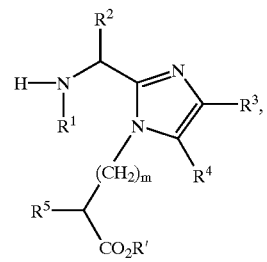

(B)

with an $N_\alpha$-protected amino acid, (Prt)-Y, where the $N_\alpha$-protected amino acid is in the form of its activated ester, anhydride or acid halide, in the presence of a base until the reaction is substantially complete to yield a compound of the formula (C),

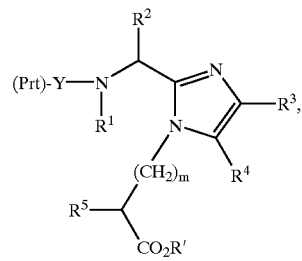

(C)

optionally deprotecting the amino group of the $N_\alpha$-protected amino acid, (Prt)-Y, using a conventional deprotecting reaction and repeating the coupling reaction with another $N_\alpha$-protected amino acid repeatedly until the desired compound of formula (I) is obtained;

Y for each occurrence is independently a D- or L-natural or unnatural α-amino acid optionally having a side chain with a protecting group;

Prt is an amine protecting group;

R' is an alkyl ester or benzyl ester;

n is 1 to 100;

and all other variables are as defined for formula (I) shown hereinabove.

In another aspect, this invention provides a process for preparing a compound of formula (I), as defined hereinabove, which comprises coupling a compound of formula (B), activated as it's active ester, anhydride, or acid halide, with an N-deprotected peptide-resin (A'), prepared by methods well known to those familiar with the peptide synthesis, deprotecting the N-terminal Fmoc group using piperidine in DMF, TAEA, or similar base and deprotecting and cleaving the resulting intermediate (B') from the resin using a strong acid. All variables are as defined for formula (I) shown hereinabove.

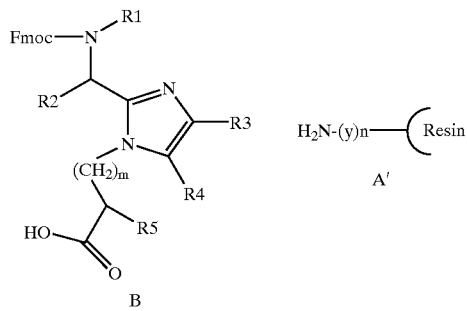

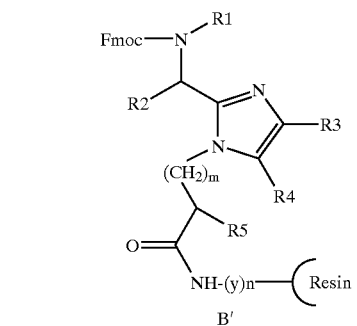

In another aspect, this invention provides, a process for preparing a compound of formula (I), which comprises coupling a compound of formula (B), activated as it's active ester, anhydride, or acid halide, with an N-deprotected peptide-resin (H), prepared by methods well known to those familiar with peptide synthesis, deprotecting the N-terminal Fmoc group using piperidine in DMF, TAEA, or similar base, acylating the liberated N-terminal amino group with an $N_\alpha$-Fmoc-protected amino acid (x) using peptide coupling reactions well known to those familiar with the art, repeating the base deprotection and coupling steps as required to incorporate additional amino acids (x), deprotecting and cleaving the resulting intermediate (C') from the resin using a strong acid. All variables are as defined for formula (I) shown hereinabove.

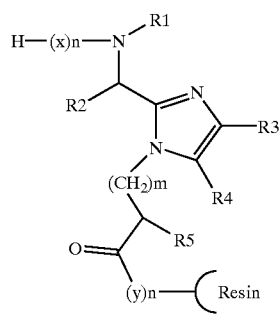

In another aspect, this invention provides a process for preparing a compound of formula (I), which comprises coupling a compound of formula (B), activated as it's active ester, anhydride, or acid halide, to an amino-substituted resin, such as Tris-(alkoxy)-benzylamine resin (PAL Resin), 4-(2',4'-Dimethoxyphenyl-aminomethyl)-phenoxy Resin (N-deprotected Rink resin), or Benzhydrylamine resin, deprotecting the N-terminal terminal Fmoc group using piperidine in DMF, TAEA, or similar base, acylating the liberated N-terminal amino group with an $N_\alpha$-Fmoc-protected amino acid (x) using peptide coupling reactions well known to those familiar with the art, repeating the base deprotection and coupling steps as required to incorporate additional amino acids (x), deprotecting and cleaving the resulting intermediate (D') from the resin using a strong acid and all other variables are as defined for formula (I) shown hereinabove. All variables are as defined for formula (I) shown hereinabove.

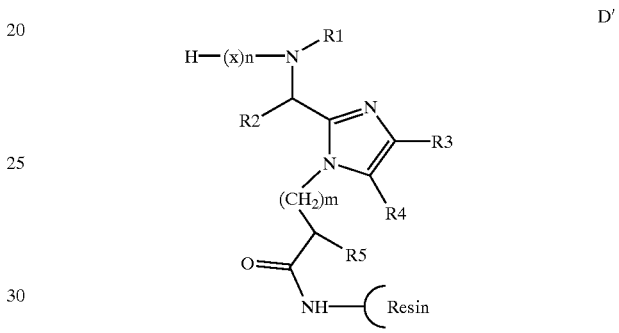

In another aspect, this invention provides a process for preparing a compound of formula (I), which comprises reacting a compound of formula (B) with a base, such as $Cs_2CO_3$, reacting the resulting phenolic cesium salt (E') with a halomethylated polystyrene resin, such as Merrifield peptide resin, removing the Fmoc protecting group with piperidine or similar organic base, acylating the liberated N-terminal amino group with an $N_\alpha$-Fmoc-protected amino acid (x) using peptide coupling reactions well known to those familiar with the art, repeating the base deprotection and coupling steps as required to incorporate additional amino acids (x), deprotecting the final protected peptide sequence at the N-terminus with piperidine or similar organic base and at the C-terminus with Tfa, cyclizing the resulting intermediate (F') using peptide coupling reactions well known to those familiar with the art, and cleaving the resulting intermediate (G') from the resin using a strong acid. All variables are as defined for formula (I) shown hereinabove.

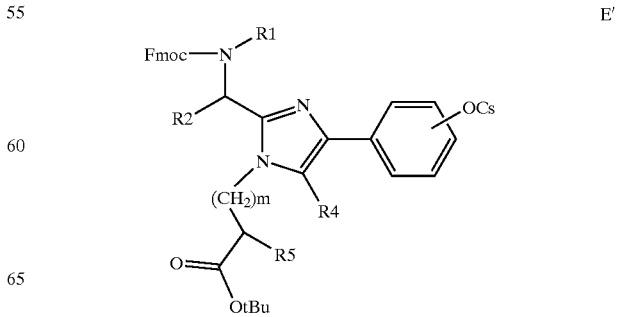

F'

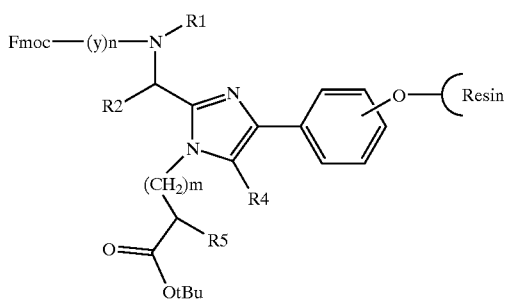

G'

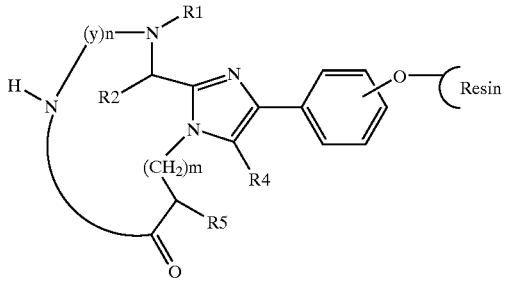

In another aspect, this invention provides a process for preparing a compound of formula (I), as defined hereinabove, which comprises coupling a compound of formula (B), activated as it's active ester, anhydride, or acid halide, with an N-deprotected peptide-resin (A'), prepared by methods well known to those familiar with the art, deprotecting the N-terminal Boc group using Tfa, and deprotecting side chain protecting groups and cleaving the resulting intermediate (H') from the resin using a strong acid such as HF. All variables are as defined for formula (I) shown hereinabove.

B

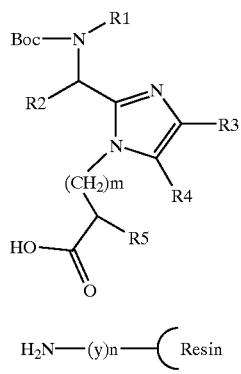

A'

H₂N—(y)n—⟨ Resin

H'

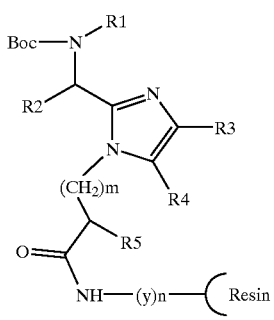

In another aspect, this invention provides a process for preparing a compound of formula (I), which comprises coupling a compound of formula (B), activated as it's active ester, anhydride, or acid halide, with an N-deprotected peptide-resin (H), prepared by methods well known to those familiar with the art, deprotecting the N-terminal Boc group using Tfa, acylating the liberated N-terminal amino group with an $N_\alpha$-Boc-protected amino acid (x) using peptide coupling reactions well known to those familiar with the art, repeating the Tfa deprotection and coupling steps as required to incorporate additional amino acids (x), deprotecting and cleaving the resulting intermediate (I') from the resin using a strong acid. All variables are as defined for formula (I) shown hereinabove.

I'

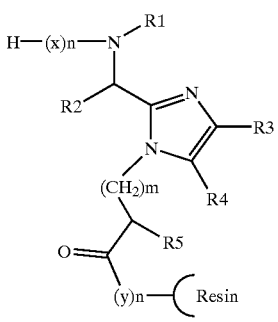

In another aspect, this invention provides a process for preparing a compound of formula (I), which comprises reacting a compound of formula (B) with a base, such as $Cs_2CO_3$, reacting the resulting phenolic cesium salt (J') with a halomethylated polystyrene resin, such as Merrifield peptide resin, removing the Boc protecting group with Tfa, acylating the liberated N-terminal amino group with an $N_\alpha$-Boc-protected amino acid (x) using peptide coupling reactions well known to those familiar with the art, repeating the Tfa deprotection and coupling steps as required to incorporate additional amino acids (x), deprotecting the final protected peptide sequence at the N-terminus with. Tfa and at the C-terminus with an inorganic base such as LiOH in aqueous DMF, cyclizing the resulting intermediate (K') with using peptide coupling reactions well known to those familiar with the art, and cleaving the resulting intermediate (L') from the resin using a strong acid. All variables are as defined for formula (I) shown hereinabove.

J'

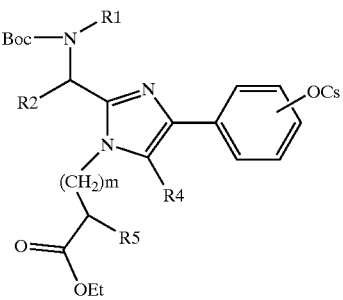

K'

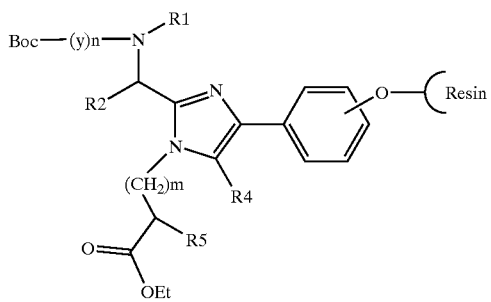

L'

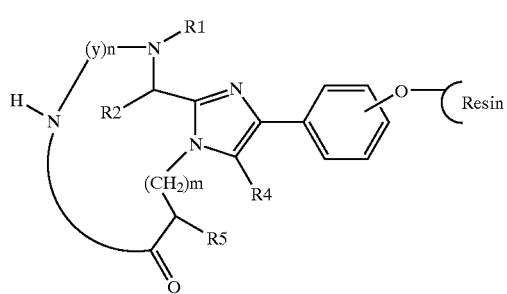

In another aspect, this invention provides a process for preparing a compound of formula (I), which comprises coupling a compound of formula (B), activated as it's active ester, anhydride, or acid halide, with an N-deprotected peptide, 4-Nitrobenzophenone oxime resin (M'), prepared by methods well known to those familiar with the art, deprotecting the N-terminal Boc group using Tfa, acylating the liberated N-terminal amino group with an $N_\alpha$-Boc-protected amino acid (x) using peptide coupling reactions well known to those familiar with the art, repeating the Tfa deprotection and coupling steps as required to incorporate additional amino acids (x), deprotecting the N-terminal Boc group with Tfa, cyclizing and cleaving the resulting intermediate N'-deprotected intermediate (N') by neutralizing with a suitable organic base, and removing side chain protecting groups with a strong acid, such as HF. All variables are as defined for formula (I) shown hereinabove.

M'

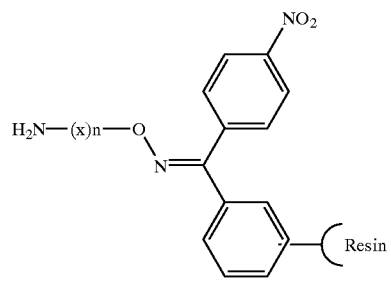

N'

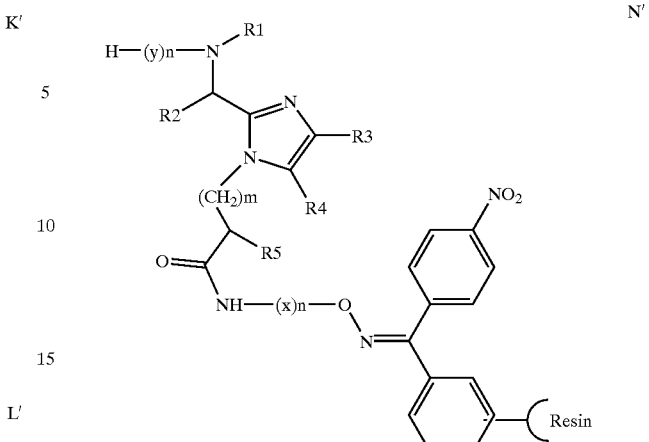

DETAILED DESCRIPTION

The term heterocycle, as used herein, represents any heterocycle that may appear in the side chain of an amino acid. Examples include, but are not limited to, such heterocycles as benzothienyl, coumaryl, imidazolyl, indolyl, purinyl, pyridyl, pyrimidinyl, quinolinyl, thiazolyl, thienyl and triazolyl.

The term aryl as used herein, is intended to mean any stable monocyclic or bicyclic carbon ring of up to 7 members in each ring, wherein at least one ring is aromatic. Examples of aryl groups include biphenyl, indanyl, naphthyl, phenyl, and 1,2,3,4-tetrahydronaphthalene.

In the instant application several abbreviated designations are used for the amino acid components, certain preferred protecting groups, reagents and solvents. The meanings of such abbreviated designations are given in Table 1.

| Abbreviated designation | | Meaning |
|---|---|---|
| Amino acids | His | L-Histidine |
| | Lys | L-Lysine |
| | Nal | L-3-(2-Naphthyl)-alanine |
| | Phe | L-Phenylalanine |
| | Ser | L-Serine |
| | Thr | L-Threonine |
| | Trp | L-Tryptophan (unless otherwise designated) |
| | Tyr | L-Tyrosine |
| | Ahx | 6-aminohexanoic acid |
| Protecting groups | Boc | 1,1-(Dimethylethoxy)carbonyl |
| | Cbz | Benzyloxycarbonyl |
| | Fmoc | 9-Fluorenylmethoxycarbonyl |
| | Trt | Triphenylmethyl |
| Solvents | DMF | N,N-Dimethylformamide |
| | THF | Tetrahydrofuran |
| | EtOAc | Ethyl acetate |
| Reagents | Tfa | Trifluoroacetic acid |
| | NMM | 4-Methylmorpholine |
| | DIEA | Diisopropylethylamine |
| | TEA | Triethylamine |
| | TAEA | Tris(2-aminoethyl)amine |
| | HOAT | 1-Hydroxy-7-azabenzotriazole |
| | HATU | [O-(7-azabenzotriazol-1-yl)-1,1,3,3-tetramethyluronium hexafluorophosphate |
| | EDC | 1-(3-Dimethylaminopropyl)-3-ethylcarbodiimide hydrochloride |
| | DCC | Dicyclohexylcarbodiimide |

In Vitro Assay

The affinity of a compound for human somatostatin subtype receptors 1 to 5 ($sst_1$, $sst_2$, $sst_3$, sst4 and $sst_5$, respectively) is determined by measuring the inhibition of [$^{125}$I-Tyr$^{11}$]SRIF-14 binding to CHO-K1 transfected cells.

The human $sst_1$ receptor gene was cloned as a genomic fragment. A 1.5 Kb PstI-XmnI segment containing 100 bp of the 5'-untranslated region, 1.17 Kb of the entire coding region, and 230 bp of the 3'-untranslated region was modified by the BglII linker addition. The resulting DNA fragment was subcloned into the BamHI site of a pCMV-81 to produce the mammalian expression plasmid (provided by Dr. Graeme Bell, Univ. Chicago). A clonal cell line stably expressing the sst, receptor was obtained by transfection into CHO-K1 cells (ATCC) using the calcium phosphate co-precipitation method (1). The plasmid pRSV-neo (ATCC) was included as a selectable marker. Clonal cell lines were selected in RPMI 1640-media containing 0.5 mg/ml of G418 (Gibco), ring cloned, and expanded into culture.

The human $sst_2$ somatostatin receptor gene, isolated as a 1.7 Kb BamHI-HindIII genomic DNA fragment and subcloned into the plasmid vector pGEM3Z (Promega), was kindly provided by Dr. G. Bell (Univ. of Chicago). The mammalian cell expression vector is constructed by inserting the 1.7 Kb BamHI-HindII fragment into compatible restriction endonuclease sites in the plasmid pCMV5. A clonal cell line is obtained by transfection into CHO-K1 cells using the calcium phosphate co-precipitation method. The plasmid pRSV-neo is included as a selectable marker.

The human $sst_3$ was isolated at genomic fragment, and the complete coding sequence was contained within a 2.4 Kb BamHI/HindIII fragment. The mammalian expression plasmid, pCMV-h3 was constructed by inserting the a 2.0 Kb NcoI-HindIII fragment into the EcoR1 site of the pCMV vector after modification of the ends and addition of EcoR1 linkers. A clonal cell line stably expressing the $sst_3$ receptor was obtained by transfection into CHO-K1 cells (ATCC) using the calcium phosphate co-precipitation method. The plasmid pRSV-neo (ATCC) was induced as a selectable marker. Clonal cell lines were selected in RPMI 1640-media containing 0.5 mg/ml of G418 (Gibco), ring cloned, and expanded into culture.

The human $sst_4$ receptor expression plasmid, pCMV-HX was provided by Dr. Graeme Bell (Univ. Chicago). The vector contains the 1.4 Kb NheI-NheI genomic fragment encoding the human $sst_4$, 456 bp of the 5'-untranslated region and 200 bp of the 3'-untranslated region, clone into the XbaI/EcoR1 sites of PCMV-HX. A clonal cell line stably expressing the $sst_4$ receptor was obtained by transfection into CHO-K1 cells (ATCC) using the calcium phosphate co-precipitation method. The plasmid pRSV-neo (ATCC) was included as a selectable marker. Clonal cell lines were selected in RPMI 1640-media containing 0.5 mg/ml of G418 (Gibco), ring cloned, and expanded into culture.

The human $sst_5$ gene was obtained by PCR using a λ genomic clone as a template, and kindly provided by Dr. Graeme Bell (Univ. Chicago). The resulting 1.2 Kb PCR fragment contained 21 base pairs of the 5'-untranslated region, the full coding region, and 55 bp of the 3'-untranslated region. The clone was inserted into EcoR1 site of the plasmid pBSSK(+). The insert was recovered as a 1.2 Kb HindIII-XbaI fragment for subcloning into pCVM5 mammalian expression vector. A clonal cell line stably expressing the $SST_5$ receptor was obtained by transfection into CHO-K1 cells (ATCC) using the calcium phosphate co-precipitation method. The plasmid pRSV-neo (ATCC) was included as a selectable marker. Clonal cell lines were selected in RPMI 1640-media containing 0.5 mg/ml of G418 (Gibco), ring cloned, and expanded into culture.

CHO-K1 cells stably expressing one of the human sst receptor are grown in RPMI 1640 containing 10% fetal calf serum and 0.4 mg/ml geneticin. Cells are collected with 0.5 mM EDTA, and centrifuged at 500 g for about 5 min. at about 4° C. The pellet is resuspended in 50 mM Tris, pH 7.4 and centrifuged twice at 500 g for about 5 min. at about 4° C. The cells are lysed by sonication and centrifuged at 39000 g for about 10 min. at about 4° C. The pellet is resuspended in the same buffer and centrifuged at 50000 g for about 10 min. at about 4° C. and membranes in resulting pellet are stored at −80° C.

Competitive inhibition experiments of [$^{125}$I-Tyr$^{11}$]SRIF-14 binding are run in duplicate in polypropylene 96 well plates. Cell membranes (10 μg protein/well) are incubated with [$^{125}$I-Tyr$^{11}$]SRIF-14 (0.05 nM) for about 60 min. at about 37° C. in 50 mM HEPES (pH 7.4), 0.2% BSA, 5 mM $MgCl_2$, 200 KIU/ml Trasylol, 0.02 mg/ml bacitracin and 0.02 mg/ml phenylmethylsulphonyl fluoride.

Bound from free [$^{125}$I-Tyr$^{11}$]SRIF-14 is separated by immediate filtration through GF/C glass fiber filter plate (Unifilter, Packard) presoaked with 0.1% polyethylenimine (P.E.I.), using Filtermate 196 (Packard) cell harvester. Filters are washed with 50 mM HEPES at about 0–4° C. for about 4 sec. and assayed for radioactivity using Packard Top Count.

Specific binding is obtained by subtracting nonspecific binding (determined in the presence of 0.1 μM SRIF-14) from total binding. Binding data are analyzed by computer-assisted nonlinear regression analysis (MDL) and inhibition constant (Ki) values are determined.

The determination of whether a compound of the instant invention is an agonist or an antagonist is determined by the following assay.

Functional Assay: Inhibition of cAMP Intracellular Production:

CHO-K1 Cells expressing human somatostatin (SRIF-14) subtype receptors are seeded in 24-well tissue culture multidishes in RPMI 1640-media with 10% FCS and 0.4 mg/ml geneticin. The medium is changed the day before the experiment.

Cells at $10^5$ cells/well are washed 2 times by 0.5 ml and fresh RPMI with 0.2% BSA supplemented with 0.5 mM (1) 3-isobutyl-1-methylxanthine (IBMX) and incubated for about 5 min at about 37° C.

Cyclic AMP production is stimulated by the addition of 1 mM forskolin (FSK) for about 15–30 minutes at about 37° C.

The agonist effect of a compound is measured by the simultaneous addition of FSK (1 μM), SRIF-14 ($1^{-12}$ M to $10^{-6}$ M) and a test compound ($10^{-10}$ M to $10^{-5}$ M).

The antagonist effect of a compound is measured by the simultaneous addition of FSK (1 μM), SRIF-14 (1 to 10 nM) and a test compound (10–10 M to $10^{-5}$ M).

The reaction medium is removed and 200 ml 0.1 N HCl is added. cAMP is measured using radioimmunoassay method (Kit FlashPlate SMP001A, New England Nuclear).

Radioligand Binding Assay

Membranes for in vitro receptor binding assays were obtained by homogenizing (Polytron, setting 6, 15 sec) the CHO-K1 cells, expressing the hsst receptor subtypes, in ice-cold 50 mM Tris-HCl and centrifuging twice at 39,000 g (10 min), with an intermediate resuspension in fresh buffer. The final pellets were resuspended in 10 mM Tris-HCl for assay. For the hsst1, hsst3, hsst4, hsst5 assays, aliquots of the membrane preparations were incubated (for about 30 min at about 37° C. with 0.05 nM [125I-Tyr11]SRIF-14 in 50 mM HEPES (pH 7.4) containing BSA (10 mg/ml); MgCl2 (5 mM)), Trasylol (200 KIU/ml), bacitracin (0.02 mg/ml), and phenylmethylsulphonyl fluoride (0.02 mg/ml). The final assay volume was 0.3 ml.

For the hsst2 assay, [125I]MK-678 (0.05 nM) was employed as the radioligand and the incubation time was about 90 min at about 25° C. The incubations were terminated by rapid filtration through GF/C filters (pre-soaked in 0.3% polyethylenimine) using a Brandel filtration manifold. Each tube and filter were then washed three times with 5-ml aliquots of ice-cold buffer.

Specific binding was defined as the total radioligand bound minus that bound in the presence of 1000 nM SRIF-14(hsst1,3,4,5), or 1000 nM MK678 for hsst2.

The compounds of the instant invention can be in vivo assayed for the uses associated with binding to the somatostatin receptor, including specificity binding to the somatostatin subtype receptor(s), according to methods well known to those skilled in the art as exemplified by the following references: I. Shimon, et. al., "Somatostatin receptor subtype specificity in human fetal pituitary cultures", J. Clin. Invest., Vol. 99, No.4, pp. 789–798, 1997; and C. Gilon, et. al., "A backbone-cyclic, receptor 5-selective somatostatin analogue: Synthesis, bioactivity, and nuclear magnetic resonance conformational analysis", J. Med. Chem. 1998, 41, 919–929.

As is well known to those skilled in the art, the known and potential uses of somatostatin agonists and/or antagonists are varied and multitudinous. These varied uses of somatostatin may be summarized as follows:

Somatostatin agonists can be used to suppress growth hormone and more particularly GH secreting adenomas (acromegaly) and TSH secreting adenomas; treat prolactin secreting adenomas; inhibit insulin and/or glucagon and more particularly diabetes mellitus, angiopathy, proliferative retinopathy, dawn phenomenon and nephropathy; inhibition of gastric acid secretion and more particularly peptic ulcers; enterocutaneous and pancreaticocutaneous fistula; irritable bowel syndrome; Dumping syndrome; watery diarrhea syndrome; AIDS related diarrhea; chemotherapy-induced diarrhea; acute or chronic pancreatitis and gastrointestinal hormone secreting tumors; treatment of cancer such as hepatoma; inhibition of angiogenesis; treatment of inflammatory disorders such as arthritis; retinopathy; chronic allograft rejection; angioplasty; preventing graft vessel and gastrointestinal bleeding.

Accordingly, the present invention includes within its scope pharmaceutical compositions comprising, as an active ingredient, at least one of the compounds of the instant invention as described herein in association with a pharmaceutically acceptable carrier.

A compound of this invention can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile Water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

Further, a compound of this invention can be administered in a sustained release composition such as those described in the following patents. U.S. Pat. No. 5,672,659 teaches sustained release compositions comprising a bioactive agent and a polyester. U.S. Pat. No. 5,595,760 teaches sustained release compositions comprising a bioactive agent in a gelable form. U.S. Pat. No. 5,821,221 teaches polymeric sustained release compositions comprising a bioactive agent and chitosan. U.S. Pat. No. 5,916,883 teaches sustained release compositions comprising a bioactive agent and cyclodextrin. U.S. application Ser. No. 09/015,394 filed Jan. 29, 1998, now abandoned, teaches absorbable sustained release compositions of a bioactive agent. The teachings of the foregoing patents and applications are incorporated herein by reference.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/kg of body weight daily are administered to humans and other animals, e.g., mammals, to obtain a therapeutic effect.

A preferred dosage range is 0.01 to 5.0 mg/kg of body weight daily which can be administered as a single dose or divided into multiple doses.

A compound of this invention can be synthesized according to the following description and Scheme I. In a first step, an amino acid, protected on the α-amino group with Boc, Cbz or other suitable group, is converted to a carboxylate salt with an inorganic base, for example NaOH, KOH, $K_2CO_3$, or most preferably $Cs_2CO_3$, in a polar solvent such as $H_2O$, DMF, THF, or the like. The solvent is removed under vacuum and the residual salt is re-dissolved in a polar aprotic solvent such as DMF and a suitable α-halo ketone is added with stirring at about −20° C. to about 100° C., most preferably at room temperature. Stirring is continued for about 10 minutes to about 24 hours, or until ester formation is complete by TLC analysis, at which time the solution is concentrated under vacuum at about 0° C. to about 100° C., most preferably at about 40° C. to about 70° C. The intermediate is re-dissolved in an aprotic organic solvent such as benzene, toluene or, most preferably, xylenes, and about 5-fold to about 100-fold or, most preferably about 15–20 fold molar excess of $NH_4OAc$ is added. The two phase mixture is heated at reflux and the polar layer is completely removed over the course of about 1 to about 4 hours by means of a Dean-Stark trap to give crude intermediate (A) which may be used crude or purified by crystallization or column chromatography.

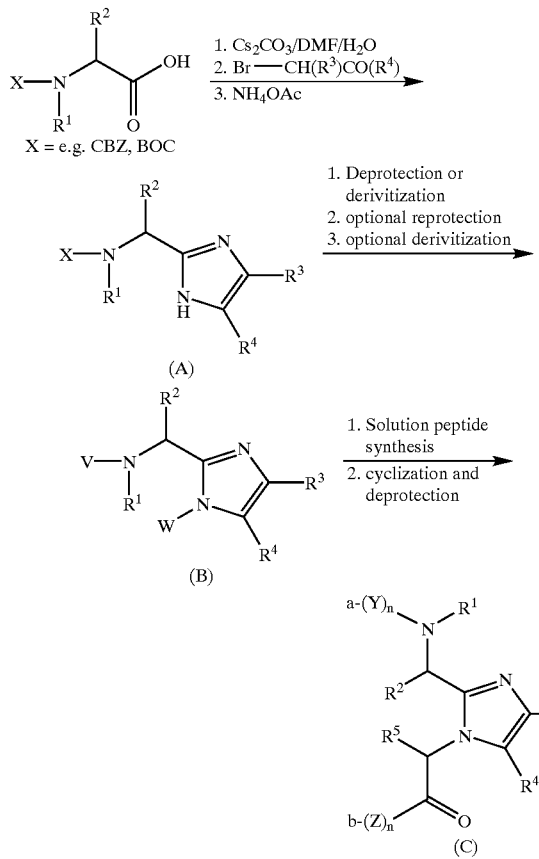

In a second step, intermediate (A) is deprotected using catalytic hydrogenation or strong acids such as HF, HCl, HBr or Tfa. The α-nitrogen may then be protected with a base sensitive protecting group such as the Fmoc group using commercially available N-(9-fluorenylmethoxycarbonyloxy)succinimide and $K_2CO_3$ in, for example, acetonitrile and water. Alternatively, the $N_\alpha$-Cbz-protected imidazole nitrogen may be alkylated with a protected carboxylic ester halide and deprotected on the α-amino group using catalytic hydrogenation to yield B' (V=H, W=—$(CH_2)_mCR^5CO_2R'$, where R' represents an alkyl or benzylic ester). The imidazole nitrogen may be protected using commercially available triphenylmethyl chloride and a tertiary amine base such as 4-methyl-morpholine, diisopropylethylamine or triethylamine to yield an Fmoc-protected intermediate which is subsequently deprotected on the α-amino group using bases such as, for example, TAEA to yield intermediate (B) (V=H, W=Trt). Alternatively, the N-deprotected imidazole B" (V=H,W=H) may be used without further modification.

In a third step, intermediate B, B', or B" is used as an anchor group for the continuous solution phase synthesis of a target peptide. Thus, the anchor group is dissolved in ethyl acetate at a concentration of about 50–200 mmol per liter and about 1 to 5 molar equivalents or, more preferably, 1.1 to 1.5 molar equivalents of an $N_\alpha$-Fmoc protected amino acid, in the form of its activated ester, anhydride or acid halide is added. The mixture is stirred over a second layer of weak base such as aqueous $Na_2CO_3$ or, more preferably, aqueous $NaHCO_3$ solution until the reaction is complete. The aqueous layer is removed and about 1 to 10 ml/mmol or, more preferably, about 2–4 ml/mmol of TAEA or piperidine is added and the mixture is stirred for about 30 minutes. The solution is then washed with saturated NaCl solution (2 times with about 30 ml/mmol) and then with 10% phosphate buffer solution adjusted to pH=5.5 (3 times with about 10 ml/mmol). Subsequent cycles are performed in a manner similar to the first cycle. The final amino acid may be protected on $N_\alpha$ with a Boc or an Fmoc group.

In a fourth step, the N-terminal and C-terminal protecting groups are removed with aqueous base or with strong acids, and the resulting peptide intermediate may be cyclized using classical peptide coupling techniques as described in "The Practice of Peptide Synthesis", Bodanszky and Bodanszky, Springer-Varlag, 1984. Accordingly, the peptide intermediate is dissolved in an aprotic solvent such as DMF and the solution is made basic by addition of tertiary amine base such as 4-methyl-morpholine. The carboxylate portion of the intermediate is activated by addition of a 1- to 6-fold molar excess of a carbodiimide, such as DCC or EDC, and an additive such as, for example, 1-hydroxybenzotriazole. The mixture is stirred at about 0° to 100° C., most preferably at about room temperature, until the reaction is complete.

In a final step, the protected peptide is freed of protecting groups using catalytic hydrogenation or strong acids such as HF, HCl, HBr or Tfa to yield final product (C), where $R^1$ to $R^5$, a, b, Y, Z, and n are as defined above for formula (I).

The infusion mass spectral data was measured on a Finnigan SSQ 7000 spectrometer equipped with an ESI (electrospray ionization) source. NMR data was obtained on a 300 MHz Varian Unity spectrometer from samples at concentrations of about 10–20 mg/ml in the designated solvents.

Alternatively, compounds of the present invention can be prepared using solid phase peptide synthesis techniques. Thus, intermediate A (X=Boc) is alkylated with, for example, ethyl bromoacetate and a suitable base, for example, $K_2CO_3$ in an aprotic solvent, for example, DMF, and the resulting ethyl ester intermediate is hydrolyzed using an aqueous base, for example, NaOH, to provide intermediate B (V=Boc, W=—$CH_2CO_2H$). Intermediate B (V=Boc, W=—$CH_2CO_2H$) can be activated using known activation techniques as described in "The Practice of Peptide Synthesis", Bodanszky and Bodanszky, Springer-Varlag, 1984, and used directly for coupling to the growing peptide on a solid support or, intermediate B (V=Boc, W=—$CH_2CO_2H$) may be attached directly to the solid support to begin a solid phase synthesis. Deprotection of the N-terminal Boc group with, for example, Tfa, allows the continuation of peptide synthesis under conditions known to one of ordinary skill in the art.

Intermediate B (V=Fmoc, W=—$CH_2CO_2$t-Bu, for example) can be treated with acid, for instance, Tfa to remove the carboxylate protecting t-butyl ester and the resulting intermediate B (V=Fmoc, W=—CH₂CO₂H, for example) can be used for solid phase peptide synthesis using the Fmoc strategy. Thus, Intermediate B (V=Fmoc, W=—CH₂CO₂H) can be activated using known activation techniques as described in "The Practice of Peptide Synthesis", M. Bodanszky and A. Bodanszky, Springer-Varlag, 1984, and used directly for coupling to the growing peptide on a solid support. Deprotection of the N-terminal Fmoc group with, for instance, piperidine allows the continuation of peptide synthesis under conditions known to one of ordinary skill in the art.

The solid phase synthesis of cyclic analogs can also be carried out, according to Scheme II, below.

SCHEME II

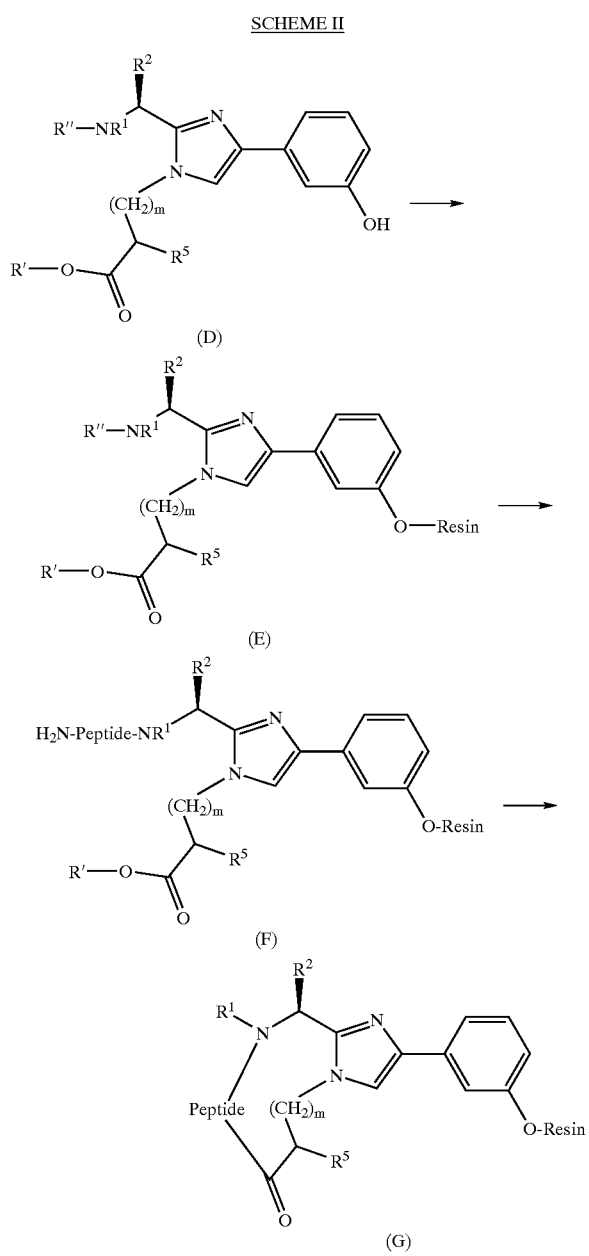

R' = alkyl, benzyl
R'' = Boc, Fmoc

Intermediate A (X=Boc or Cbz, R³=2-methoxyphenyl, 3-methoxyphenyl or 4-methoxyphenyl) can be treated with 1M BBr₃ in CH₂Cl₂ for about ½ hour to provide the free phenol A (X=H, R³=2-hydroxyphenyl, 3-hydroxyphenyl or 4-hydroxyphenyl). The nitrogen may then be protected with an acid sensitive protecting group such as the Boc group using di-t-butyldicarbonate and a base, for example, NaOH in a mixture of an organic, water miscible solvent, for example, dioxane and water. Intermediate A (X=Boc, R³=2-hydroxyphenyl, 3-hydroxyphenyl or 4-hydroxyphenyl) is alkylated with, for example, ethyl bromoacetate and a suitable base, for example, K₂CO₃ in an aprotic solvent, for example, DMF, to provide the resulting ethyl ester intermediate D. Intermediate D is then converted to it's cesium salt by the action of cesium carbonate. The cesium salt is reacted, in excess, with Merrifield resin to provide intermediate E. Intermediate E is subject to elaboration using standard Boc solid phase peptide synthesis or standard Fmoc solid phase synthesis as previously described to yield intermediate F. When the complete amino acid sequence has been constructed, the C-terminal ethyl ester is unmasked using a suitable base, for example, LiOH in aqueous DMF and the peptide is cyclized using standard activation protocol, for example, a carbodiimide with, for example, hydroxybenzotriazole and a tertiary amine base, for example, diisopropylethyl amine to provide intermediate G. Final side chain deprotection and cleavage from the resin is realized by addition of a very strong acid, for example, HF to yield compounds of the invention.

The present invention is illustrated by the following examples, but it is not limited to the details thereof.

EXAMPLE 1

Cyclo[Tyr-D-Trp-Lys-Val-PheΨ(4-(3-Methoxyphenyl)imidazole)-Gly]

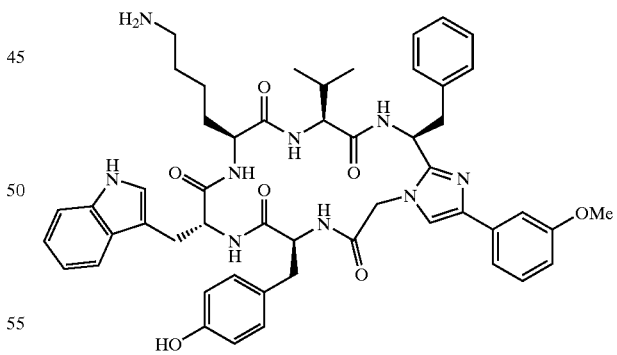

Example 1 was synthesized according to synthetic scheme 1 as shown below:

Example 1 was synthesized according to synthetic scheme 1 as shown below:

SCHEME 1

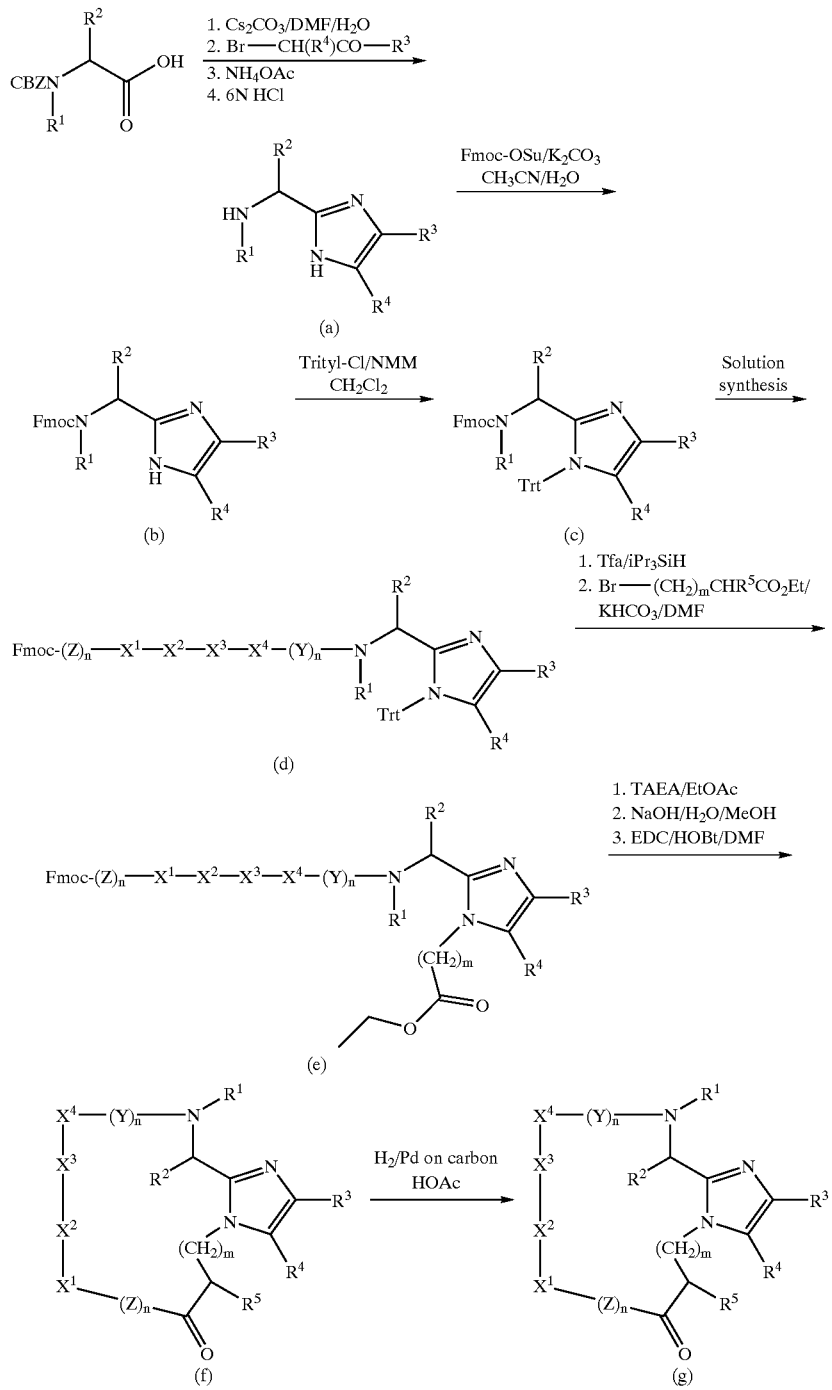

Step a: 2-(1-(S)-Amino-2-phenylethyl)-4-(3-methoxyphenyl)-imidazole

Cbz-(L)-Phenylalanine (10.0 g, 33.4 mmol) and CS₂CO₃ (5.44 g, 16.7 mmol) were combined in 2:1/DMF:H₂O (75 ml) and the mixture was swirled until homogeneous. Solvents were removed under reduced pressure, the residue was dissolved in DMF (70 ml) and 2-bromo-3'-methoxyacetophenone (7.65 g, 33.4 mmol) in DMF (30 ml) was added. The mixture was stirred for about 30 min. at room temperature then concentrated under reduced pressure. The resulting keto-ester was dissolved in xylenes (150 ml) and the CsBr was filtered off. Ammonium acetate (40.0 g, 0.52 mole) was added and the mixture was heated at reflux for about 2 hours with removal of excess NH₄OAc and liberated H₂O using a Dean-Stark trap. The reaction was cooled and washed with saturated NaHCO₃ solution (50 ml) and saturated NaCl solution (50 ml). The xylenes layer was dried over Na₂SO₄, filtered and concentrated under vacuum.

The residue was dissolved with dioxane (30 ml), 6N HCl (115 ml) was added and the mixture heated at reflux for about 3 hours. The solution was concentrated under vacuum and triturated with ethyl ether (4×100 ml). The residue was dried to constant weight under vacuum to yield 12.15 g (99%) of intermediate 1a, mass spec. 294.2 MH+.

Step b: 2-(1-(S)-((Fluorenylmethoxy)carbonyl)amino-2-phenylethyl)-4-(3-methoxyphenyl)-imidazole Intermediate 1a (11.8 g, 32.2 mmol) was dissolved in 1:1/acetonitrile:$H_2O$ (200 ml) and $K_2CO_3$ (5.38 g, 39 mmol) was cautiously added in portions. 9-Fluorenylmethyl-succinimidylcarbonate was added and the resulting mixture was stirred vigorously for about 20 minutes. Product was extracted with EtOAc (100 ml) and the EtOAc layer was washed with $H_2O$ (2×50 ml). The EtOAc layer was dried over $Na_2SO_4$, filtered and concentrated under vacuum. The product was purified by flash chromatography on silica gel (150 g) eluting with 2:2:1/$CH_2Cl_2$:hexanes:EtOAc and then with 1:1/hexanes:EtOAc. Product fractions were pooled and concentrated under vacuum to a yield intermediate 1b as a pale yellow foam, 14.77 g (85%). Mass spec. 516.3 MH+, NMR (300 MHz, DMSO-d6), 11.8–12.0 (1H, s), 7.8–8.0 (3H, d), 7.6–7.8 (2H, d), 7.5 (1H, s), 7.1–7.5 (12H, m), 6.7–6.9 (1H, d) 4.8–5.0 (1H, m), 4.1–4.3 (3H, m), 3.7–3.9 (3H, s), 3.0–3.4 (2H, m).

Step c: 2-(1-(S)-((Fluorenylmethoxy)carbonyl)amino-2-phenylethyl)-4-(3-methoxyphenyl)-1-triphenylmethyl-imidazole Intermediate 1b (13.9 g, 26.9 mmol) was dissolved in $CH_2Cl_2$ (50 ml) under $N_2$, 4-methylmorpholine (2.96 ml, 26.9 mmol) and chlorotriphenylmethane (7.51 g, 26.9 mmol) were added and the solution was allowed to stir at room temperature for about 45 minutes. Solids were removed by filtration and the filtrate purified by flash chromatography on silica gel (300 g) using 70:30/hexanes:EtOAc as eluant. Product fractions were combined and concentrated under vacuum to yield intermediate 1c as a foam, 18.0 g (88%), NMR (300 MHz, DMSO-d6), 7.84–7.95 (2H, d), 7.7–7.8 (1H, d), 7.6–7.7 (1H, d), 6.7–7.5 (29H, m), 4.34.5 (1H, m), 3.75–3.95 (2H, m) 3.75–3.85 (3H, s), 3.6–3.7 (1H, m), 2.65–2.85 (1H, d, d), 2.05–2.2 (1H, m).

Step d: 2-(1-(S)-((Fmoc-Tyr(OBzl)-D-Trp-Lys(Cbz)-Val)amino-2-phenylethyl)-4-(3-methoxyphenyl)-1-(triphenylmethyl)-imidazole Intermediate 1c (1.89 g, 2.50 mmol) was dissolved in EtOAc (40 ml), Tris(2-aminoethyl)amine (9 ml) was added and the mixture stirred vigorously for about ½ hour. The EtOAc layer was washed with saturated NaCl solution (2×120 ml) and then with 10% phosphate buffer solution adjusted to about pH=5.5 (3×40 ml). The EtOAc layer was stirred over saturated $NaHCO_3$ solution (40 ml) and Fmoc-Val-F (1.02 g, 3.00 mmole) was added. The reaction was stirred for about 1 hour and the aqueous layer was removed.

The intermediate was then sequentially deprotected and coupled with Fmoc-Lys(Cbz)-OSu, Fmoc-D-Trp-OSu and Fmoc-Tyr(OBzl)OSu in a manner similar to the Fmoc-Val-F cycle described immediately above. The EtOAc layer was diluted with 1.5 volumes of hexanes and applied to a silica gel column for purification by flash chromatography using 50:30:20/$CH_2Cl_2$:EtOAc:hexanes first and then with 4:1/EtOAc:hexanes as eluants. Product fractions were pooled and concentrated under vacuum to yield intermediate 1d as a white foam, 1.90 g, (46%). Mass spec 1581.2 MNa+, 1559.5 MH+.

Step e: 1-((2-Ethoxy-2-oxo)ethyl)-2-(1-(S)-((Fmoc-Tyr(OBzl)-D-Trp-Lys(Cbz)-Val)amino-2-phenylethyl)-4-(3-methoxyphenyl)-imidazole Intermediate 1d (519 mg, 0.33 mmol) was dissolved in Tfa (10 ml) containing $iPr_3SiH$ (205 ul, 1.0 mmol) and the mixture was stirred for about 15 minutes. Intermediate was precipitated by addition of ethyl ether (60 ml) and filtered off. Mass spec 1316 MH+. The intermediate was dissolved in DMF (3 ml), $KHCO_3$ (198 mg, 2.0 mmol) and ethyl bromoacetate (721 ul, 6.5 mmol) were added and the mixture was stirred overnight at room temperature. The mixture was concentrated under vacuum, dissolved in $CH_2Cl_2$ (10 ml) and washed with $H_2O$ (10 ml). The $CH_2Cl_2$ layer was dried over $Na_2SO_4$, filtered and concentrated under vacuum to yield crude intermediate 1e (540 mg) which was used without further purification.

Step f: Cyclo[Tyr(OBzl)-D-Trp-Lys(Cbz)-Val-PheΨ(4-(3-methoxyphenyl)imidazole)-Gly]

Intermediate 1e (540 mg, 0.33 mmol) was suspended in EtOAc (10 ml) and tris(aminoethyl)amine (1 ml) was added and the mixture was stirred vigorously for about ½ hour. EtOAc (10 ml) was added and the solution was washed with saturated NaCl solution (2×25 ml) and then with 10% phosphate buffer solution (pH=5.5, 3×10 ml). The intermediate was precipitated by addition of hexanes (40 ml), and the solvents were decanted. The residue dissolved in methanol (10 ml) and stirred overnight at room temperature with 2.5N NaOH (0.5 ml). The mixture was diluted to turbidity with $H_2O$ and the pH was adjusted to about 6.7. The deprotected intermediate was filtered off and dried under vacuum. The solid was taken up in DMF (25 ml) and DCC (340 mg, 1.65 mmol) and HOBt (252 mg, 1.65 mmol) were added. The mixture was stirred at room temperature for about 2 hours and concentrated under reduced pressure. Crude product was purified by flash chromatography on silica gel using EtOAc as eluant. Product fractions were combined and concentrated under vacuum to yield intermediate 1f as a glass. (180 mg, 48% from intermediate 1d). Mass spec 1134.5 MH+.

Step g: Cyclo[Tyr-D-Trp-Lys-Val-PheΨ(4-(3-methoxyphenyl)imidazole)-Gly]

Intermediate 1f (180 mg, 0.16 mmol) was dissolved in acetic acid (10 ml) containing 10% Pd on carbon (24 mg) and the mixture was shaken under $H_2$ (25 psi) at room temperature for about 8 hours. The catalyst was filtered off and the residue concentrated under vacuum. The crude mixture was composed of completely deprotected material (both Cbz and benzyl ether removed) and partially deprotected material (Cbz removed and benzyl ether intact). The mixture was purified by preparative HPLC on a VYDAC® Protein & Peptide $C_{18}$ column (The Nest Group Inc., Southborough, Mass.) using a gradient of 20% to 70% $CH_3CN$/0.1% Tfa over about 55 minutes. Pure fractions of the more polar peak were combined, concentrated, and lyophilized (2×10 ml 0.5% HCl, then 1×10 ml $H_2O$) to yield the title compound of Example 1, 45 mg (29%). Mass spec. 910.4 MH+.

EXAMPLE 2

Cyclo[Tyr(OBzl)-D-Trp-Lys-Val-PheΨ(4-(3-methoxyphenyl)imidazole)-Gly]

Example 2 was prepared substantially according to synthetic scheme 1, Example 1, but using the appropriate amino acids. Pure fractions of the less polar peak from the purification of 1 g were combined, concentrated, and lyophilized (2×10 ml 0.5% HCl, then 1×10 ml $H_2O$) to yield the title product of Example 2, 33 mg (21%). Mass spec. 1000.4 MH+.

EXAMPLE 3

Cyclo[Trp-D-Trp-Lys-Val-PheΨ(4-(3-methoxyphenyl)imidazole)-Gly]

Example 3 was prepared according to synthetic scheme 1 in a manner substantially similar to Example 1 but with the following differences:

Step d: 2-(1-(S)-((Fmoc-Trp-D-Trp-Lys(Cbz)-Val-)amino-2-phenylethyl)-4-(3-methoxyphenyl)-1-(triphenylmethyl)-imidazole Intermediate 1c (757 mg, 1.0 mmol) was dissolved in EtOAc (20 ml), tris(2-aminoethyl)amine (3 ml) was added and the mixture stirred vigorously for about ½ hour. The EtOAc layer was washed with saturated NaCl solution (2×60 ml) and then with 10% phosphate buffer solution adjusted to a pH of about 5.5 (3×20 ml). The EtOAc layer was stirred over saturated $NaHCO_3$ solution (20 ml) and Fmoc-Val-F (825 mg, 2.33 mmol) was added. The reaction was stirred for about 1 hour and the aqueous layer was removed.

The intermediate was sequentially deprotected and coupled with Fmoc-Lys(Cbz)OSu, Fmoc-D-Trp-OSu and Fmoc-Trp-OSu in a manner similar to the Fmoc-Val-F cycle described immediately above. The EtOAc layer was diluted with 1.5 volumes of hexanes and applied to a silica gel column for purification by flash chromatography using 50:30:20/$CH_2Cl_2$:EtOAc:hexanes first and then with 4:1/EtOAc:hexanes as eluants. Product fractions were pooled and concentrated under vacuum to yield intermediate 3d as a white foam, 1.02 g, (68%). Mass spec 11492.0 MNa+, 1514.2 MH+.

Step e: 1-((2-Ethoxy-2-oxo)ethyl)-2-(1-(S)-((Fmoc-Trp-D-Trp-Lys(Cbz)-Val-)amino-2-phenylethyl)-4-(3-methoxyphenyl)-imidazole Intermediate 3d (1.00 g, 0.67 mmol) was dissolved in a mixture of $CH_2Cl_2$ (10 ml), Tfa (1 ml) and $iPr_3SiH$ (205 ul, 1.0 mmol) and the mixture was stirred for about 20 minutes. A mixture of 1:1/$Et_2O$:hexanes (100 ml) was added and the intermediate was filtered off and dried (0.88 g). The intermediate was dissolved in DMF (10 ml), $KHCO_3$ (200 mg, 2.00 mmole) and ethyl bromoacetate were added and the reaction was stirred overnight at room temperature. The mixture was concentrated under reduced pressure to yield intermediate 3e which was used without further purification. Mass spec 1335.7 MH+

Step f: Cyclo[Trp-D-Trp-Lys(Cbz)-Val-PheΨ(4-(3-methoxyphenyl)imidazole)-Gly]

Intermediate 3e (crude, 0.67 mmol) was dissolved in methanol (10 ml) and stirred at room temperature with 2.5N NaOH (1.0 ml) for about 45 minutes. The mixture was diluted to turbidity with $H_2O$ and the pH was adjusted to 6.9. Solvents were decanted and the residue as triturated with $H_2O$ to yield a pale yellow powder (650 mg, mass spec 1085.5 MH+). The powder (629 mg) was dissolved in DMF (20 ml) then NMM (220 ul, 2.0 mmol), EDC (192 mg, 1.0 mmol) and HOBt (153 mg, 1.0 mmol) were added. The mixture was stirred at room temperature for about 2 hours and concentrated under vacuum. Crude product was dissolved in $CH_2Cl_2$ (15 ml) and washed with 10% phosphate buffer solution (adjusted to pH=5.5). The $CH_2Cl_2$ layer was dried over $Na_2SO_4$, filtered and concentrated to 2 ml. Ethyl ether was added to precipitate the product, which was filtered off and dried to yield intermediate 3f (440 mg, 71%). Mass spec 1067.4 MH+.

Step g: Cyclo[Trp-D-Trp-Lys-Val-PheΨ(4-(3-methoxyphenyl)imidazole)-Gly]

Intermediate 3f (200 mg, 0.19 mmol) was dissolved in acetic acid (15 ml) containing 10% Pd on carbon (40 mg) and the mixture was shaken under $H_2$ (25 psi) at room temperature for 2 days. The catalyst was filtered off and the residue concentrated under vacuum. The crude mixture was purified by preparative HPLC on a $C_{18}$ column (Rainin Microsorb™ 80–220-C5) using a gradient of 20% to 70% $CH_3CN$/0.1% Tfa over about 55 minutes. A second pass using a gradient of 30% to 50% $CH_3CN$/0.1% Tfa over about 55 minutes was required to obtain good separation. Pure fractions were combined, concentrated, and lyophilized (2×10 ml 0.5% HCl, then 1×10 ml $H_2O$) to yield the title compound of Example 3, 26 mg (14%). Mass spec. 933.5 MH+.

EXAMPLE 4

Cyclo[Trp-D-Trp-Lys-Val-PheΨ(4-(3-hydroxyphenyl)imidazole)-Gly]

Example 4 was prepared according to synthetic scheme 1 in a manner substantially similar to that of Example 1 with the following differences:

Step q: Cyclo[Trp-D-Trp-Lys-Val-PheΨ(4-(3-hydroxyphenyl)imidazole)-Gly]

Intermediate 3f (150 mg, 0.14 mmol) was dissolved in $CH_2Cl_2$ (12 ml) and a solution of 1M BBr3 in hexanes was added under $N_2$. The resulting slurry was stirred for about ½ hour. Methanol (10 ml) was added and the mixture was concentrated under vacuum. The crude mixture was purified by preparative HPLC on a $C_{18}$ column using a gradient of 24% to 48% $CH_3CN$/0.2% $NH_4OAc$ over about 50 minutes. Pure fractions were combined, concentrated, and lyophilized (2×10 ml $H_2O$) to yield the title compound of Example 4, 40 mg (29%). Mass spec. 919.4 MH+.

EXAMPLE 5

Cyclo[Trp-D-Trp-Lys-Thr(OBzl)-PheΨ(4-(3-methoxyphenyl)imidazole)-Gly]

Example 5 was prepared according to scheme 1 in a manner substantially similar to Example 3 except that Fmoc-Thr(OBzl)-F was used in place of Fmoc-Val-F in step d. Mass spec 1025.5 MH+.

EXAMPLE 6

Cyclo[Trp-D-Trp-Lys-Thr-PheΨ(4-(3-hydroxyphenyl)imidazole)-Gly]

Example 6 was prepared according to scheme 1 in a manner substantially analogous to Example 4 except that intermediate 5f, cyclo[Trp-D-Trp-Lys(Cbz)-Thr(OBzl)-PheΨ(4-(3-methoxyphenyl)imidazole)-Gly], was used in place of intermediate 3f in step g. Mass spec 1025.5 MH+.

EXAMPLE 7

H-Trp-D-Trp-Lys-Abu-PheΨ(4-(3-hydroxyphenyl)imidazole)-Gly-OH

Example 7 was prepared according to scheme 1 in a manner substantially analogous to Example 3 except that Fmoc-Abu-F was used in place of Fmoc-Val-F in step 3d and cyclization with carbodiimide and HOBt was not performed in step 3f. Mass spec 937.3 MH+.

EXAMPLE 8

Cyclo[Trp-D-Trp-Lys-Abu-PheΨ(4-(3-hydroxyphenyl)imidazole)-Gly]

Example 8 was prepared according to scheme 1 in a manner substantially analogous to Example 3 except that Fmoc-Abu-F was used in place of Fmoc-Val-F in step 3d. Mass spec 919.5 MH+.

EXAMPLE 9

Cyclo[Phe-D-Trp-Lys-Tyr(OBzl)-PheΨ(4-(1,1-dimethylethyl)imidazole)-Gly]

Example 9 was prepared according to Scheme 2.

SCHEME 2

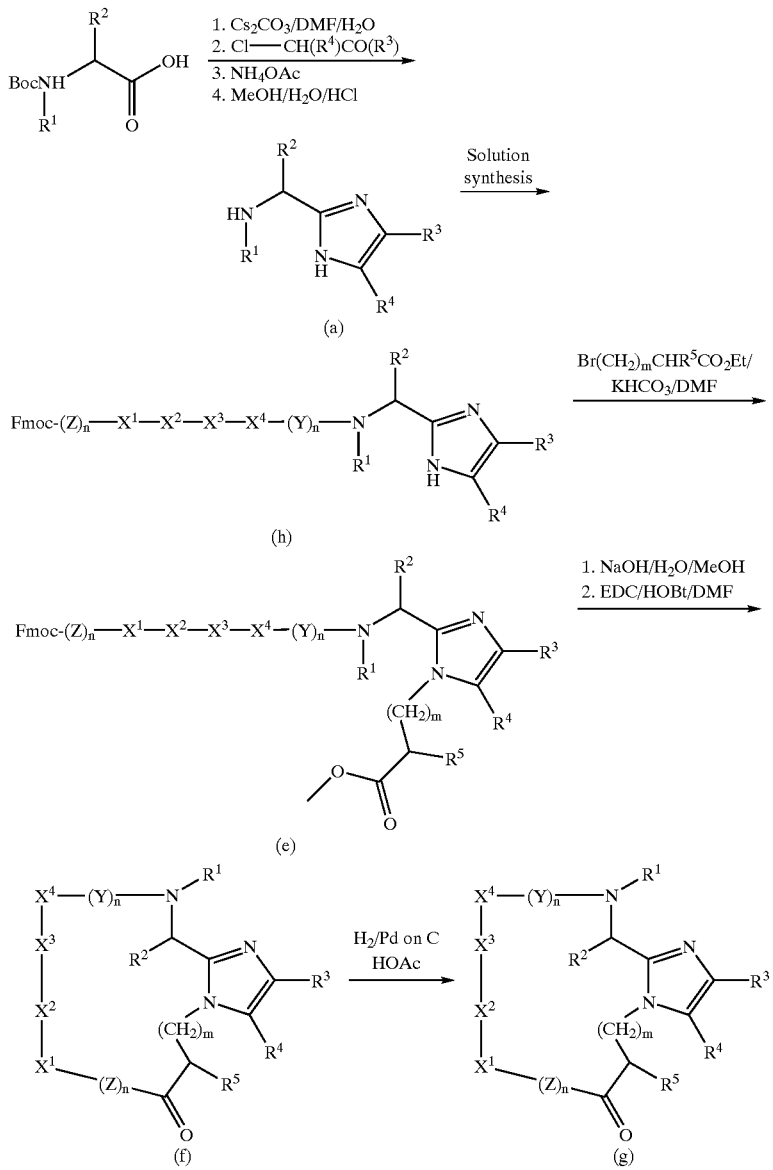

Step a. 2-(1-(S)-Amino-2-phenylethyl)-4-(1,1-dimethylethyl)-imidazole

Boc-(L)-Phenylalanine (5.31 g, 20.0 mmol) and Cs$_2$CO$_3$ (3.26 g, 10.0 mmol) were combined in 1:1/DMF:H$_2$O (50 ml) and the mixture was swirled until a homogeneous mixture was obtained. Solvents were removed under reduced pressure and the residue was dissolved in DMF (50 ml) and 1-chloropinacolone (2.63 ml, 20.0 mmol) was added. The mixture was stirred overnight at room temperature then concentrated under reduced pressure. The resulting ketoester was dissolved in xylenes (100 ml) and the CsBr was filtered off. Ammonium acetate (25.0 g, 0.33 mol) was added and the mixture was heated at reflux for about 2 hours with removal of excess NH$_4$OAc and liberated H$_2$O using a Dean-Stark trap. The reaction was cooled and washed with saturated NaHCO$_3$ solution (50 ml), dried over Na$_2$SO$_4$, filtered and concentrated under vacuum. Purification of the protected intermediate by flash chromatography on silica gel using 80:20/hexanes:EtOAc as eluant yielded 3.45 g (50%) of a crystalline intermediate (Mass spec 344.3 MH+). This intermediate was dissolved with methanol (30 ml), and conc. HCl (5.0 ml) was added and the mixture stirred for about 3 hours. The solution was concentrated under vacuum and the residue precipitated from THF and ethyl ether. The solid was dried under vacuum to yield 1.89 g (95%) of intermediate 9a. NMR (300 MHz, DMSO-d6), 8.5–10.5 (3H, broad s), 7.3–7.4 (1H, s), 7.15–7.35 (3H, m), 7.0–71 (2H, m), 4.9–5.1 (1H, t), 3.5–3.65 (2H, d), 1.2–1.3 (9H, s).

Step h. 2-(1-(S)-((Fmoc-Phe-D-Trp-Lys(Boc)-Tyr(OBzl))-amino-2-phenylethyl)-4-(1,1-dimethylethyl)-1H-imidazole Intermediate 9a (790 mg, 2.50 mmol) was dissolved in EtOAc (40 ml), tris(2-aminoethyl)amine (9 ml) was added and the mixture stirred vigorously for about ½ hour. The EtOAc layer was washed with saturated NaCl solution (2×120 ml) and then with 10% phosphate buffer solution adjusted to about pH=5.5 (3×40 ml). The EtOAc layer was stirred over saturated NaHCO$_3$ solution (40 ml) and FmocTyr(OBzl)-OSu (1.02 g, 3.00 mmol) was added. The reaction was stirred for about 1.5 hour and the aqueous layer was removed.

The intermediate was sequentially deprotected and coupled with Fmoc-Lys(Cbz)-OSu, Fmoc-D-Trp-OSu and Fmoc-Phe-OSu in a manner similar to the Fmoc-Tyr(OBzl)-OSu cycle described immediately above. The EtOAc layer was applied to a silica gel column for purification by flash chromatography using 1% acetic acid/EtOAc as eluant. Product fractions were pooled and concentrated under vacuum. The crude product was redissolved in EtOAc, precipitated by addition of hexanes and filtered off. The solid was dried under vacuum to yield intermediate 9h, 1.67 g, (52%). Mass spec 1280.7 MH+.

Step e: 4-(1,1-Dimethylethyl)-2-(1-(S)-((Fmoc-Phe-D-Trp-Lys(Boc)-Tyr(OBzl)-)amino-2-phenylethyl)-1-(2-ethoxy-2-oxo-ethyl)-imidazole Intermediate 9h (128 mg, 0.10 mmol) was dissolved in DMF (2 ml), $K_2CO_3$ (35 mg, 0.25 mmol) and ethyl bromoacetate (28 ul, 0.25 mmol) were added and the mixture was stirred overnight at room temperature. The mixture was concentrated under vacuum, dissolved in EtOAc (10 ml) and washed with $H_2O$ (10 ml). The EtOAc layer was dried over $Na_2SO_4$, filtered and concentrated under vacuum to yield crude intermediate 9e (126 mg, 92%) which was used without further purification.

Step f: Cyclo[Phe-D-Trp-Lys(Boc)-Tyr(OBzl)-PheΨ(4-(3-methoxyphenyl)imidazole)-Gly]

Intermediate 9e (1 16 mg, 0.085 mmol) was suspended in EtOAc (2 ml) and tris(aminoethyl)amine (0.5 ml) was added and the mixture was stirred vigorously for about ½ hour. EtOAc (10 ml) was added and the solution was washed with saturated NaCl solution (2×5 ml) and then with 10% phosphate buffer solution (pH=5.5, 3×5 ml). The intermediate was precipitated by addition of hexanes (40 ml), and the intermediate was filtered off (76 mg). The residue was dissolved in methanol (2 ml) and stirred overnight at room temperature with 2.5N NaOH (0.1 ml). The mixture was diluted to turbidity with $H_2O$ and the pH was adjusted to about 6.0. The deprotected intermediate was filtered off and dried under vacuum. The solid was taken up in DMF (20 ml) and DCC (126 mg, 0.60 mmole) and HOBt (90 mg, 0.60 mmol) were added. The mixture was stirred at room temperature for about 6 hours and concentrated under vacuum. Dissolved in EtOAc (5 ml) and washed with saturated $NaHCO_3$ solution (1×5 ml) and saturated NaCl solution (5 ml). Dried over $Na_2SO_4$, filtered and concentrated under vacuum to yield intermediate 9f. Mass spec 1098.5 MH+.

Step g: Cyclo[Phe-D-Trp-Lys-Tyr-PheΨ(4-(1,1-dimethylethyl)imidazole)-Gly]

Intermediate 9f (crude, 0.085 mmol) was dissolved in Tfa (9.4 ml) containing $iPr_3SiH$ and $H_2O$ (0.5 ml), stirred for about 20 minutes and concentrated under vacuum. The crude mixture was purified by preparative HPLC on a $C_{18}$ column using a gradient of 30% to 60% $CH_3CN$/0.1% Tfa over about 50 minutes. A second pass using a gradient of 32% to 80% $CH_3CN$/0.2% $NH_4OAc$ over about 50 minutes was required to obtain good separation. Pure fractions were combined, concentrated, and lyophilized (2×10 ml 0.5% HCl, then 1×10 ml $H_2O$) to yield the title compound of Example 9, 9 mg (10%). Mass spec. 998.4 MH+.

EXAMPLE 10

Cyclo[Phe-D-Trp-Lys-Val-PheΨ(4-(3-methoxyphenyl)imidazole-Gly]

Example 10 was prepared according to scheme 1 in a manner analogous to Example 3 except that Fmoc-Phe-OSu was used in place of Fmoc-Trp-F in step d.

Mass spec. 894.4 MH+.

EXAMPLE 11

Cyclo[Phe-D-Trp-Lys-Tyr(OBzl)-PheΨ(4-(3-methoxyphenyl)imidazole-Gly]

Example 11 was prepared according to scheme 1 in a manner analogous to Example 3 except that Fmoc-Phe-OH was used in place of Fmoc-Trp-F and Fmoc-Tyr(OBzl)-OH was used in place of Fmoc-Val-F in step d. The Fmoc-Tyr(OBzl)-OH was activated with DCC and commercially available HOAt. The crude mixture in step g was composed of completely deprotected material (both Cbz and benzyl ether removed) and partially deprotected material (Cbz removed and benzyl ether intact). The less polar peak resulting from partial deprotection yielded the title compound of Example 11. Mass spec 1048.5 MH+.

EXAMPLE 11

Cyclo[Phe-D-Trp-Lys-Tyr-PheΨ(4-(3-methoxyphenyl)imidazole-Gly]

Example 12 was prepared according to scheme 1 in a manner analogous to Example 3 except that Fmoc-Phe-OH was used in place of Fmoc-Trp-F and Fmoc-Tyr(OBzl)-OH was used in place of Fmoc-Val-F in step d. The Fmoc-Tyr(OBzl)-OH was activated with DCC and commercially available HOAt. The crude mixture in step g was composed of completely deprotected material (both Cbz and benzyl ether removed) and partially deprotected material (Cbz removed and benzyl ether intact). The more polar peak resulting from complete deprotection yielded the title compound of Example 12. Mass spec 958.4 MH+.

EXAMPLE 13

Cyclo[Phe-D-Trp-Lys-Tyr-PheΨ(4-(3-hydroxyphenyl)imidazole-Gly]

Example 13 was prepared according to scheme 1 in a manner analogous to Example 4 except that intermediate 11f, cyclo[Phe-D-Trp-Lys(Cbz)-Tyr(OBzl)-PheΨ(4-(3-methoxyphenyl)imidazole-Gly] was used in place of intermediate 3f in step g. Mass spec 944.6 MH+.

EXAMPLE 14

Cyclo[Trp-D-Trp-Lys-Tyr(Bzl)-PheΨ(4-(3-methoxyphenyl)imidazole-Gly]

Example 14 was prepared according to Scheme 2 in a manner substantially analogous to Example 9 with the following differences:

Step h: 2-(1-(S)-((Fmoc-Trp-D-Trp-Lys(Cbz)-Tyr(Bzl))-amino)-2-phenylethyl)-4-(3-methoxyphenyl)-1-(triphenylmethyl)-imidazole Peptide synthesis was performed in a manner analogous to step 9h except Fmoc-Trp-OSu was used in place of Fmoc-Phe-OSu, Fmoc-Lys(Boc)-OSu was used in place of Fmoc-Lys(Cbz)-OSu and Fmoc-Tyr(Bzl)-OSu was used in place of Fmoc-Val-OSu. Yield=783 mg (57%), Mass spec=1370.6 MH+.

Step e: 1-((2-Ethoxy-2-oxo)ethyl)-2-(1-(S)-((Fmoc-Trp-D-Trp-Lys(Boc)-Tyr(OBzl))-amino)-2-phenylethyl)-(3-methoxyphenyl)-imidazole Alkylation of intermediate 14h was accomplished in a manner similar to reaction 9h yield=640 mg (80%), mass spec=1456.3 MH+.

Step f: Cyclo[Trp-D-Trp-Lys(Boc)-Tyr(Bzl)-PheΨ(4-(3-methoxyphenyl)imidazole)-Gly]

Intermediate 14e (640 mg, 0.44 mmol) was dissolved in 15 ml methanol and 2.5N NaOH (1 ml, 2.5 mmol) was added. The mixture was stirred for about ½ hour and then the pH was adjusted to about 7.0 by addition of 5% HCl solution. The methanol was removed under reduced pressure and the aqueous layer decanted. The residue was thoroughly dried under reduced pressure then dissolved in 15 ml DMF. DCC (206 mg, 1.0 mmol) and HOBt (153 mg, 1.0 mmol) were added and the reaction allowed to stir overnight. The reaction was concentrated under vacuum, dissolved in EtOAc (10 ml) and washed twice with 10% phosphate buffer, pH=5.5. The EtOAc layer was then applied to a silica gel column and the product eluted with more EtOAc. Product fractions were combined and concentrated to 240 mg (46%) of intermediate 14f.

Step a: Cyclo[Trp-D-Trp-Lys-Tyr(Bzl)-PheΨ(4-(3-methoxyphenyl)imidazole)-Gly]

Intermediate 14f (240 mg, 0.20 mmol) was dissolved in $CH_2Cl_2$ (10 ml) and Tfa (10 ml) containing $iPr_3SiH$ (205 ul, 1.0 mmol) was added. The mixture was stirred at room temperature for about 15 minutes. The $CH_2Cl_2$ was evaporated under reduced pressure and the crude product was precipitated by addition of ether. Solvents were decanted and the residue was further purified by preparative HPLC on a $C_{18}$ column using a gradient of 30% to 50% $CH_3CN$/0.1% Tfa over about 55 minutes. Pure fractions were combined, concentrated and lyophilized (2×10 ml 0.5% HCl, then 1×10 ml $H_2O$) to yield the title compound of Example 14, 25 mg (11%). Mass spec. 1087.4 MH+.

EXAMPLE 15

Cyclo[-Tyr-D-Trp-Lys-Val-PheΨ(4-(3-hydroxyphenyl)imidazole-Gly]

Example 15 was prepared according to synthetic scheme 1 in a manner substantially analogous to Example 4 with the following exception:
Step g: Cyclo[Tyr-D-Trp-Lys-Val-PheΨ(4-(3-hydroxyphenyl)imidazole)-Gly]

Intermediate 1f (130 mg, 0.115 mmol) was dissolved in $CH_2Cl_2$ (5 ml) and a solution of 1M $BBr_3$ in hexanes (5 ml) was added under $N_2$. The resulting slurry was stirred for about ½ hour then cooled to about 0° C. Methanol (10 ml) was added and the mixture was concentrated under vacuum. The crude mixture was applied to a $C_{18}$ column, washed with 1% $NH_4OAc$ solution, washed with 0.1% Tfa solution and then eluted using a gradient of 20% to 35% $CH_3CN$/0.1% Tfa over about 50 minutes. Pure fractions were combined, concentrated, and lyophilized (2×10 ml 0.5% HCl) to yield the title compound of Example 15, 60 mg (54%). Mass spec. 896 MH+.

EXAMPLE 16

Cyclo[Phe-D-Trp-Lys-NaI-PheΨ(4-(3-hydroxyphenyl)imidazole-Gly]

Example 16 was prepared according to scheme 1 in a manner substantially analogous to Example 3 with the following differences:
Step d: 2-(1-(S)-((Fmoc-Phe-D-Trp-Lys(Cbz)-NaI-)amino)-2-phenylethyl)-4-(3-methoxyphenyl)-1-(triphenylmethyl)-imidazole Intermediate 16d was prepared in a manner substantially similar to intermediate 1d except that Fmoc-NaI-OAt was used in place of Fmoc-Val-F and Fmoc-Phe-OH was used in place of Fmoc-Tyr(Bzl)-OH.
Step g: Cyclo[Tyr-D-Trp-Lys-Val-PheΨ(4-(3-hydroxyphenyl)imidazole)-Gly]

Step 16g was carried out in a manner substantially analogous to step 4g to yield the title compound of Example 16. Mass spec.

EXAMPLE 17

Cyclo[Phe-D-Trp-Lys-NaI-PheΨ(4-(3-methoxyphenyl)imidazole-Gly]

Example 17 was prepared according to scheme 1 in a manner substantially analogous to Example 16 with the following exceptions:
Step g: Cyclo[Tyr-D-Trp-Lys-Val-PheΨ(4-(3-methoxyphenyl)imidazole)-Gly]

Intermediate 17f (310 mg, 0.27 mmol) was suspended in anisole (3 ml) and the suspension was treated with about 12 ml anhydrous HF. The mixture was stirred for about 1 hour at about 0° C. The HF was distilled off and the product precipitated by addition of ether. The crude product was filtered off and further purified by preparative HPLC using a gradient of 20–80% $CH_3CN$/0.1% Tfa over about 40 minutes. Pure fractions were combined, concentrated and lyophilized twice from dilute HCl solution. Yield=56 mg (19%), Mass spec. 992.4 MH+.

SCHEME 3

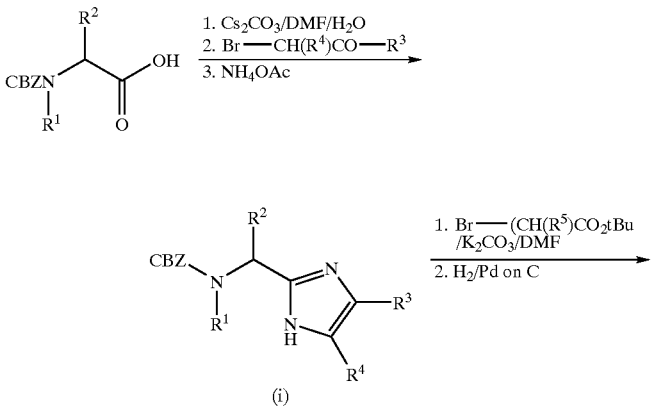

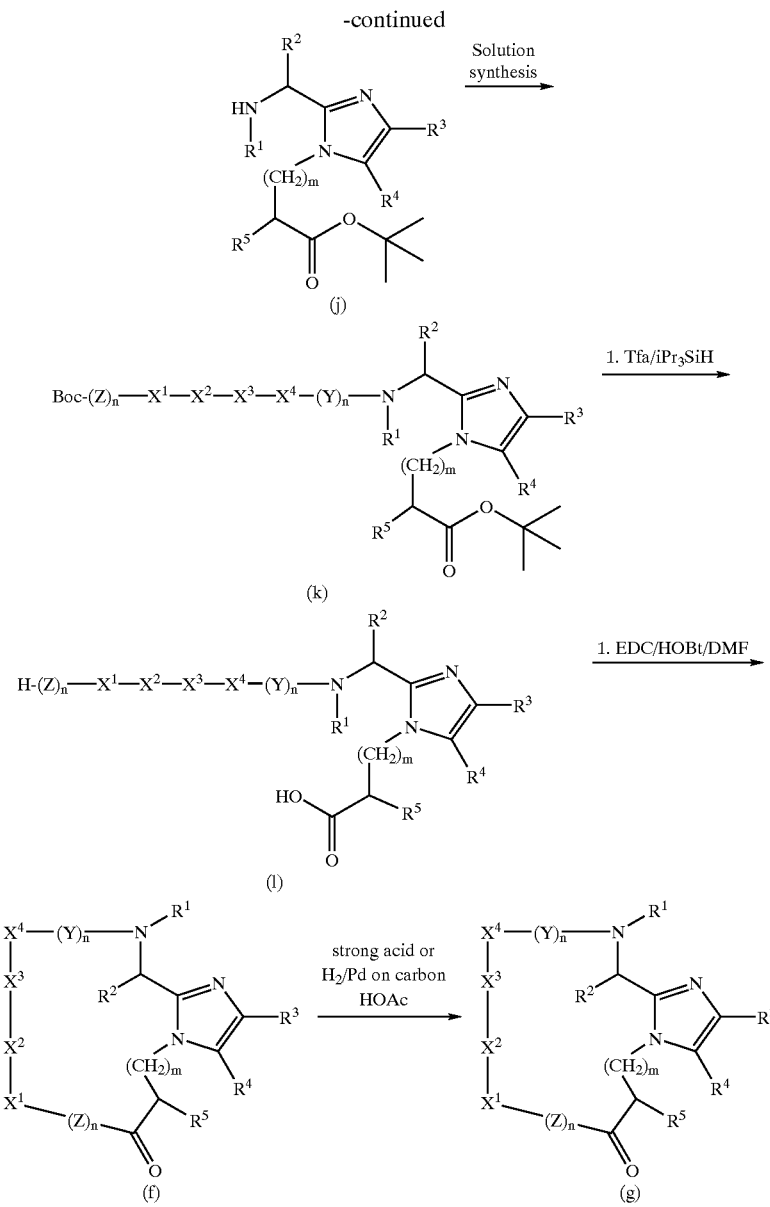

EXAMPLE 18

Cyclo[Trp-D-Trp-Lys-Tyr(Bzl)-PheΨ(4-(3-methoxyphenyl)imidazole-(γ)Abu]

Example 18 was prepared according to synthetic scheme 3.

Step i: 2-(1-(S)-((Phenylmethoxy)carbonyl)-amino-2-phenylethyl)-4-(4-methoxyphenyl)-imidazole Cbz-(L)-Phenylalanine (10.0 g, 33.4 mmol) and $Cs_2CO_3$ (5.44 g, 16.7 mmol) were combined in 2:1/DMF:$H_2O$ (75 ml) and the mixture was swirled until homogeneous. Solvents were removed under reduced pressure, the residue was dissolved in DMF (70 ml) and 2-bromo-3'-methoxyacetophenone (7.65 g, 33.4 mmol) in DMF (30 ml) was added. The mixture was stirred for about ½ hour at room temperature then concentrated under reduced pressure. The resulting keto-ester was dissolved in xylenes (150 ml) and the CsBr was filtered off. Ammonium acetate (40.0 g, 0.52 mol) was added and the mixture was heated at reflux for about 2 hours with removal of excess $NH_4OAc$ and liberated $H_2O$ using a Dean-Stark trap. The reaction was cooled and washed with saturated $NaHCO_3$ solution (50 ml) and saturated NaCl solution (50 ml). The xylenes layer was dried over $Na_2SO_4$, filtered and concentrated under vacuum to yield intermediate 18i as a tan solid (13.8 g, 96%). Mass spec. 428.2 (MH+).

Step j: 2-(1-(S)-Amino-2-phenylethyl)-1-(4-(1,1-dimethylethoxy)-4-oxo-butyl)-4-(4-methoxyphenyl)-imidazole Intermediate 18i (2.14 g, 5.0 mmol) was dissolved in DMF (11.5 ml) and treated with $KHCO_3$ (1.50 g, 15.0 mmol) and 4-bromo-t-butylbutyrate (6.69 g, 30 mmol) in three portions with stirring at about 50° C. for about 18 hours. The mixture was diluted with ether and washed once with saturated $NaHCO_3$ solution and once with saturated NaCl solution. The ether layer was dried over $Na_2SO_4$, filtered and concentrated to an oil. Column chromatography on silica gel using $CH_2Cl_2$ as eluant yielded product as an oil.

The crude alkylated product was deprotected by hydrogenation in acetic acid using 10% Pd on carbon as catalyst. The catalyst was filtered off and solvents evaporated under reduced pressure. The residue was dissolved in EtOAc and washed with saturated NaHCO$_3$ solution and saturated NaCl solution, dried over Na$_2$SO$_4$ and concentrated to yield intermediate 18j as an oil (450 mg) which was used in the next step without further purification.

Step k: 2-(1-(S)-((Boc-Trp-D-Trp-Lys(Cbz)-Val)-amino-2-phenylethyl)-1-((4-(1,1-dimethylethoxy)-4-oxo)butyl)-4-(3-methoxyphenyl)-imidazole The solution synthesis was performed in a manner analogous to the synthesis detailed in step 1d except that Boc-Trp-OSu was used in place of Fmoc-Tyr(OBzl)-OSu and Fmoc-Tyr(OBzl)-OAt was used in place of Fmoc-Val-F to yield intermediate 18k. Yield=1.03 g (81%).

Step l: 2-(1-(S)-((H-Trp-D-Trp-Lys(Cbz)-Val)-amino-2-phenylethyl)-1-((4-hydroxy-4-oxo)butyl)-4-(3-methoxyphenyl)-imidazole Intermediate 18k was treated with a solution containing (iPr)$_3$SiH (593 ul, 2.90 mmol) in Tfa (10 ml) and stirred for about one hour. The reaction was concentrated and triturated with 1:1 ether:hexanes solution to yield intermediate 18l as a tan solid which was used in the next step without further purification. Mass spec. 1267.7 MH+.

Step f: Cyclo[Trp-D-Trp-Lys(Cbz)-Tyr(Bzl)-PheΨ(4-(3-methoxyphenyl)imidazole-(γ)Abu]

Intermediate 18l was dissolved in DMF (20 ml) and 4-methylmorpholine (159 ul, 1.45 mmol), HOBt (196 mg, 1.45 mmol) and EDC (278 mg, 1.45 mmol) were added and the reaction was stirred overnight. The reaction was concentrated under vacuum and purified by flash chromatography on silica gel using CH$_2$Cl$_2$:MeOH (9:1) as eluant to yield intermediate 18f. Yield=220 mg (24%). Mass spec. 1249.7 MH+.

Step g: Cyclo[Trp-D-Trp-Lys-Tyr(Bzl)-PheΨ(4-(3-methoxyphenyl)imidazole-(γ)Abu]

Intermediate 18f (220 mg, 176 umol) was partially hydrogenated in acetic acid under 30 psi of H$_2$ at room temperature using 10% Pd on C as catalyst for about 14 hours. The catalyst was filtered off and the filtrate concentrated under vacuum. The crude mixture was purified by preparative HPLC on a C$_{18}$ column using a gradient of 0% to 75% CH$_3$CN/0.1% Tfa over 40 minutes. Pure fractions of the product peak were combined, concentrated, and lyophilized (2×10 ml 0.5% HCl, then 1×10 ml H$_2$O) to yield the title compound of Example 18, 72 mg (37%). Mass spec. 1115.6 MH+.

EXAMPLE 19

Cyclo[Trp-D-Trp-Lys-Tyr(Bzl)-PheΨ(4-(4-methoxyphenyl)imidazole-Gly]

Example 19 was prepared according to Scheme 3 in a manner substantially similar to Example 18 with the following differences:

Step j: 2-(1-(S)-Amino-2-phenylethyl)-1-(2-(1,1-dimethylethoxy)-2-oxo-ethyl)-4-(4-methoxyphenyl)-imidazole Intermediate 18i (854 mg, 2.0 mmol) was dissolved in DMF (10 ml) and tert-Butyl bromoacetate (646 ul, 4.0 mmol) and K$_2$CO$_3$ (552 mg, 4.0 mmol) were added and the reaction was stirred at room temperature overnight. Solvents were removed under reduced pressure and the residue dissolved in EtOAc and washed with saturated NaCl solution. The EtOAc layer was dried over Na$_2$SO$_4$, filtered and concentrated under vacuum to yield 1.02 g foam. Mass spec. 428.2 MH+, NMR (300 MHz, DMSO-d6), 7.85–8.0 (1H, d), 7.6–7.75 (2H, d), 7.85–7.95 (1H, s), 7.1–7.35 (10H, m), 6.9–7.0 (2H, d), 4.75–5.05 (5H, m), 3.7–3.9 (3H, s), 3.1–3.4 (2H, m), 1.3–1.5 (9H, s).

The intermediate white foam (1.02 g, 1.88 mmol) was dissolved in HOAc (50 ml) containing 10% Pd on C (50 mg) and hydrogenated at room temperature under 30 psi of H$_2$ for 10 hours. Catalyst was filtered off and 2N HCl (940 uL, 1.88 mmol) was added. The mixture was lyophilized once and then re-lyophilized from 20% CH$_3$CN/H$_2$O to yield intermediate 19j as a light brown solid (862 mg,) which was used without further purification. Mass spec. 408.2 MH+.

Step g: Catalytic hydrogenation and work-up performed in a manner substantially analogous to step 18g yielded the title product (22 mg, 4%) as a white solid. Mass spec. 1088.2 MH+.

EXAMPLE 20

Cyclo[(Trp-D-Trp-Lys-Tyr(Bzl)PheΨ(4-(phenyl) imidazole-Gly]

Example 20 was prepared according to Scheme 3 in a manner substantially analogous to Example 18 except that 2-bromoacetophenone was used in place of 2-bromo-3'-methoxyacetophenone in step i. Mass spec. 1057.4 MH$^+$.

EXAMPLE 21

Cyclo[Trp-D-Trp-Lys-Tyr(Bzl)-PheΨ(4-(3-methoxyphenyl)imidazole-(ε)Ahx]

Example 21 was prepared according to Scheme 3 in a manner substantially analogous to Example 18 with the following differences:

Step j: 2-(1-(S)-Amino-2-phenylethyl)-1-(6-(ethoxy)-6-oxo-hexyl)-4-(3-methoxyphenyl)-imidazole Intermediate 21i (855 mg, 2.0 mmol) was dissolved in DMF (8.0 ml) and treated with KHCO$_3$ (200 mg, 2.0 mmol) and ethyl 6-bromohexanoate (3.56 ml, 20 mmol) at about 120° C. for about 8 hours. The mixture was concentrated and the residue was purified by column chromatography on silica gel using 2:1/hexanes:EtOAc as eluant to yield pure product as a gum (0.94 g).

The crude alkylated product was deprotected by hydrogenation in acetic acid using 10% Pd on carbon as catalyst. The catalyst was filtered off and solvents evaporated under reduced pressure. The residue was dissolved in dilute HCl, frozen and lyophilized to yield intermediate 21j as a pale yellow solid, (720 mg, 91%) which was used in the next step without further purification. Mass spec. 436.2 MH+.

Step k and step l: 2-(1-(S)-((H-Trp-D-Trp-Lys(Boc)-Tyr (OBzl)-2-(1-(S)-amino-2-phenylethyl)-1-(6-(ethoxy)-6-oxo-hexyl)-4-(3-methoxyphenyl)-imidazole Fmoc-Tyr(OBzl)-OAt-was prepared by mixing Fmoc-Tyr (OBzl)-OH (493 mg, 1.00 mmol), HOAt (136 mg, 1.0 mmol) and DCC (206 mg, 1.0 mmol) in 8 ml EtOAc for about ½ hour then filtering off the dicyclohexylurea. The resulting solution was added to a solution of intermediate 21j (457 mg, 0.9 mmole) in EtOAc (4 ml) and the mixture was stirred over saturated NaHCO$_3$ solution (10 ml) until the reaction was complete by mass spectral analysis. The aqueous layer was removed and the EtOAc layer was dried over Na2SO4, filtered and treated with tris(2-aminoethyl)amine (2.7 ml). The mixture was stirred vigorously for about ½ hour. The EtOAc layer was washed with saturated NaCl solution (2×60 ml) and then with 10% phosphate buffer the solution was adjusted to about pH=5.5 (3×15 ml).

The intermediate was sequentially deprotected and coupled with Fmoc-Lys(Cbz)-OSu, Fmoc-D-Trp-OSu and Fmoc-Trp-OSu in a manner substantially similar to the Fmoc-Tyr(OBzl)OAt cycle described immediately above. A final Fmoc deprotection yielded the N-terminally deprotected intermediate ethyl ester. The EtOAc layer was dried over $Na_2SO_4$, filtered and diluted with 4 volumes of hexanes. Solvents were poured off and the residue was triturated with hexanes to yield product as solid (0.67 g, 58%) which was used without further purification. Mass spec. 1289.6 MH+.

The ethyl ester was removed by treatment of intermediate in MeOH (5.0 ml) with 1.7M NaOH solution (1.7 ml) overnight. The mixture was adjusted to about pH=8.2 with 5% HCl solution and the solvents were removed under reduced pressure. The residue was taken up in DMF, the NaCl was removed by filtration and the DMF solution was taken to the next step without further purification.

Cyclization and deprotection were carried out in a manner analogous to Example 18 to yield the title compound of Example 21 as a white powder, 62 mg. Mass spec. 1143.9 MH+.

EXAMPLE 22

Cyclo[Trp-D-Trp-Lys-Tyr(Bzl)-PheΨ(4-(3-hydroxyphenyl)imidazole-(γ)Abu]

Example 22 was prepared according to Scheme 3 in a manner substantially analogous to Example 18 with the following differences:
Step j: 2-(1-(S)-Amino-2-phenylethyl)-1-(4-(ethoxy)-4-oxobutyl)-4-(4-hydroxyphenyl)imidazole Intermediate 22i (2.0 g, 4.68 mmol) was dissolved in DMF (7.0 ml) and treated with $KHCO_3$ (468 mg, 4.68 mmol) and ethyl 4-bromo-butyrate (6.70 ml, 46.8 mmol) and stirred at about 100° C. for about 30 hours. The mixture was diluted with ether and washed once with saturated $NaHCO_3$ solution and once with saturated NaCl solution. The ether layer was dried over $Na_2SO_4$, filtered and concentrated to an oil. Column chromatography on silica gel using $CH_2Cl_2$ as eluant yielded product as an oil (2.53 g, 94%). Mass spec. 542.3 $MH^+$.

The crude alkylated product (2.53 g, 4.67 mmol) in $CH_2Cl_2$ (50 ml) was added dropwise over about 15 minutes at about −10° C. to a solution of 1M $BBr_3$/hexanes (23.4 ml) in $CH_2Cl_2$ (250 ml). The mixture was allowed to warm to room temperature and stirred for about 2 hours. Ethanol (40 ml) was added and the mixture was concentrated to about 50 ml. The solution was diluted with ethanol (100 ml) and allowed to stir overnight at room temperature. The mixture was concentrated under reduced pressure and the residue was distributed between EtOAc and saturated $NaHCO_3$ solution. The EtOAc layer was dried over $Na_2SO_4$, filtered and concentrated under reduced pressure to an oil (1.41 g, 76%), which was used in subsequent steps without protection of the phenol. Mass spec. 394.3 $MH^+$.

HPLC Retention Times

| Example No. | HPLC system | Retention time (minutes) |
|---|---|---|
| 1 | A | 13.65 |
| 2 | A | 18.50 |
| 3 | A | 16.03 |
| 4 | B | 6.97 |
| 5 | C | 20.41 |
| 6 | C | 11.75 |
| 7 | D | 9.53 |
| 8 | B | 11.02 |
| 9 | E | 7.69 |
| 10 | J | 6.02 |
| 11 | F | 4.18 |
| 12 | G | 4.11 |
| 13 | H | 5.50 |
| 14 | G | 6.16 |
| 15 | I | 17.03 |
| 16 | K | 9.12 |
| 17 | J | 8.11 |
| 18 | J | 8.86 |
| 19 | L | 6.47 |
| 20 | M | 6.65 |
| 21 | G | 8.14 |
| 22 | N | 12.10 |

HPLC Systems:
A. Gradient: 20–80% $CH_3CN$/0.1% Tfa, 24 min.
  Flow rate: 1.0 ml/min.
  Detection: 254 nm
  Column: VYDAC® Protein and Peptide C18
B: Gradient: 35–50% $CH_3CN$/0.1% Tfa, 24 min.
  Flow rate: 1.0 ml/min.
  Detection: 254 nm
  Column: VYDAC® Protein and Peptide C18
C: Gradient: 32–64% $CH_3CN$/0.1% NH4OAc, 24 min.
  Flow rate: 1.0 ml/min.
  Detection: 254 nm
  Column: VYDAC® Protein and Peptide C18
D: Gradient: 20–60% $CH_3CN$/0.1% Tfa, 24 min.
  Flow rate: 1.0 ml/min.
  Detection: 254 nm
  Column: VYDAC® Protein and Peptide C18
E: Gradient: 55–75% $CH_3CN$/0.1% Tfa, 24 min.
  Flow rate: 1.0 ml/min.
  Detection: 220 nm
  Column: Phenomenex LICHROSPHERE® 5 RP18 (Phenomenex, 2320 W 205th St., Torrance, Calif.)
F: Gradient: 60% $CH_3CN$/0.1% Tfa, isocratic
  Flow rate: 1.0 ml/min.
  Detection: 254 nm
  Column: VYDAC® Protein and Peptide C18
G: Gradient: 50% $CH_3CN$/0.1% Tfa, isocratic
  Flow rate: 1.0 ml/min.
  Detection: 254 nm
  Column: VYDAC® Protein and Peptide C18
H: Gradient: 38% $CH_3CN$/0.1% Tfa, isocratic
  Flow rate: 1.0 ml/min.
  Detection: 254 nm
  Column: VYDAC® Protein and Peptide C18
  Gradient: 20–40% $CH_3CN$/0.1% Tfa, 24 min.
  Flow rate: 1.0 ml/min.
  Detection: 254 nm
  Column: VYDAC® Protein and Peptide C18
J: Gradient: 50% $CH_3CN$/0.1% Tfa, isocratic
  Flow rate: 1.0 ml/min.
  Detection: 254 nm
  Column: NUCLEOSIL™ C18, 5 micron (Alltech Associates, 2051 Waukegan Rd., Deerfield, Ill.)

K: Gradient: 40% CH₃CN/0.1% Tfa, isocratic
  Flow rate: 1.0 ml/min.
  Detection: 254 nm
  Column: NUCLEOSIL™ C18, 5 micron
L: Gradient: 52% CH₃CN/0.1% Tfa, isocratic
  Flow rate: 1.0 ml/min.
  Detection: 254 nm
  Column: NUCLEOSIL™ C18, 5 micron
M: Gradient: 50% CH3CN/0.1% Tfa, isocratic
  Flow rate: 1.0 ml/min
  Detection: 254 nm
  Column: NUCLEOSIL™ C18, 5 micron
N: Gradient: 48% CH3CN/0.1% Tfa, isocratic
  Flow rate: 1.0 ml/min
  Detection: 254 nm
  Column: NUCLEOSIL™ C18, 5 micron

What is claimed is:

1. A compound of the formula (I),

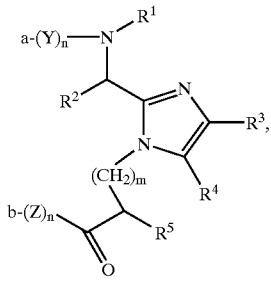

(I)

or a pharmaceutically acceptable salt thereof, wherein,

Y and Z for each occurrence are each independently a D- or L-natural or unnatural α-amino acid;

n for each occurrence is independently 0 to 50, provided that both n cannot be 0 at the same time;

m is 0 or an integer from 1 to 10;

a is H or $R^1$;

b is OH, —$OR^1$ or —$NR^9R^9$;

or a is taken together with b to form an amide bond;

$R^1$ is independently H, $(C_1-C_4)$alkyl or aryl-$(C_1-C_4)$alkyl;

$R^2$ is H or an optionally substituted moiety selected from the group consisting of $(C_1-C_4)$alkyl, phenyl, phenyl-$(C_1-C_4)$alkyl and heterocyclyl-$(C_1-C_4)$alkyl; where the optionally substituted moiety is optionally substituted by one or more substituents each independently selected from the group consisting of $(C_1-C_4)$alkyl, $(C_3-C_8)$cycloalkyl, —O—$R^6$, —S(O)$_q$—$R^7$, —N($R^9R^9$), —NHCO—$R^6$, —NHSO$_2R^9$, —CO$_2R^9$, —CONR$^9R^9$ and —SO$_2NR^9R^9$, where q is 0, 1, 2 or 3;

$R^3$ and $R^4$ are each independently H, halo or an optionally substituted moiety selected from the group consisting of $(C_1-C_4)$alkyl, $(C_3-C_8)$cycloalkyl, aryl and aryl-$(C_1-C_4)$alkyl; where the optionally substituted moiety is optionally substituted by one or more substituents selected from the group consisting of OH, $(C_1-C_4)$alkyl, $(C_1-C_4)$alkoxy, aryloxy, aryl-$(C_1-C_4)$alkoxy, —NR$^9R^9$, COOH, —CONR$^9R^9$ and halo;

or $R^3$ and $R^4$ are taken together with the carbons to which they are attached to form optionally substituted aryl, where the aryl is optionally substituted by one or more substituents each independently selected from the group consisting of OH, $(C_1-C_4)$alkyl, $(C_1-C_4)$alkoxy, aryloxy, aryl-$(C_1-C_4)$alkoxy, —NR$^9R^9$, COOR$^5$, —CONR$^9R^9$ and halo;

$R^5$ for each occurrence is independently H, or an optionally substituted moiety selected from the group consisting of $(C_1-C_4)$alkyl and aryl-$(C_1-C_4)$alkyl, where the optionally substituted moiety is optionally substituted by one or more substituents each independently selected from the group consisting of $(C_1-C_4)$alkyl, OH, $(C_1-C_4)$alkoxy, aryloxy, NO$_2$, aryl-$(C_1-C_4)$alkoxy, —NR$^9R^9$, COOH, —CONR$^9R^9$ and halo;

$R^6$ for each occurrence is independently selected from the group consisting of H, $(C_1-C_4)$alkyl, $(C_1-C_4)$alkoxy, aryl-$(C_1-C_4)$alkyl and aryl-$(C_1-C_4)$alkoxy;

$R^7$ is H when q is 3 or, $R^7$ for each occurrence is independently selected from the group consisting of $(C_1-C_4)$alkyl, aryl and aryl-$(C_1-C_4)$alkyl when q is 0, 1 or 2; and $R^9$ for each occurrence is independently selected from the group consisting of H, NO$_2$, $(C_1-C_4)$alkyl, aryl and aryl-$(C_1-C_4)$alkyl.

2. A compound of the formula (II),

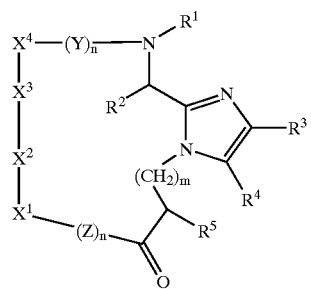

(II)

or a pharmaceutically acceptable salt thereof, wherein,

Y and Z for each occurrence are each independently a D- or L-natural or unnatural α-amino acid;

m is 0 or an integer from 1 to 10;

n for each occurrence is independently 0 to 6;

$R^1$ for each occurrence is independently H, $(C_1-C_4)$alkyl or aryl-$(C_1-C_4)$alkyl;

$R^2$ is H or an optionally substituted moiety selected from the group consisting of $(C_1-C_4)$alkyl, phenyl, phenyl-$(C_1-C_4)$alkyl and heterocyclyl-$(C_1-C_4)$alkyl, where the optionally substituted moiety is optionally substituted by one or more substituents each independently selected from the group consisting of $(C_1-C_4)$alkyl, cycloalkyl, —O—$R^6$, —S(O)$_q$—$R^7$, —N($R^9R^9$), —NHCO—$R^6$, —NHSO$_2R^9$, —CO$_2R^9$, —CONR$^9R^9$ and —SO$_2NR^9R^9$, where q is 0, 1, 2 or 3;

$R^3$ and $R^4$ are each independently H, halo or an optionally substituted moiety selected from the group consisting of $(C_1-C_4)$alkyl, cycloalkyl, aryl and aryl-$(C_1-C_4)$alkyl; where the optionally substituted moiety is optionally substituted by one or more substituents selected from the group consisting of OH, $(C_1-C_4)$alkyl, $(C_1-C_4)$alkoxy, aryloxy, aryl-$(C_1-C_4)$alkoxy, —NR$^9R^9$, COOH, —CONR$^9R^9$ and halo;

or $R^3$ and $R^4$ are taken together with the carbons to which they are attached to form optionally substituted aryl, where the aryl is optionally substituted by one or more substituents each independently selected from the group consisting of OH, $(C_1-C_4)$alkyl, $(C_1-C_4)$alkoxy, aryloxy, aryl-$(C_1-C_4)$alkyl, —$NR^9R^9$, $COOR^5$, —$CONR^9R^9$ and halo;

$R^5$ for each occurrence is independently H, or an optionally substituted moiety selected from the group consisting of $(C_1-C_4)$alkyl and aryl-$(C_1-C_4)$alkyl, where the optionally substituted moiety is optionally substituted by one or more substituents each independently selected from the group consisting of $(C_1-C_4)$alkyl, OH, $(C_1-C_4)$alkoxy, aryloxy, $NO_2$, aryl-$(C_1-C_4)$alkoxy, —$NR^9R^9$, COOH, —$CONR^9R^9$ and halo;

$R^6$ for each occurrence is independently selected from the group consisting of H, $(C_1-C_4)$alkyl, $(C_1-C_4)$alkoxy, aryl-$(C_1-C_4)$alkyl and aryl-$(C_1-C_4)$alkoxy;

$R^7$ is H when q is 3, or $R^7$ for each occurrence is independently selected from the group consisting of $(C_1-C_4)$alkyl, aryl and aryl-$(C_1-C_4)$alkyl when q is 0, 1 or 2; and $R^9$ for each occurrence is independently selected from the group consisting of H, $NO_2$, $(C_1-C_4)$alkyl, aryl and aryl-$(C_1-C_4)$alkyl, $X^1$ is a natural or unnatural D- or L-α-amino acid, where when $X^1$ is Phe, NaI, Trp, Tyr, PaI or His the aromatic ring thereof is optionally substituted on carbon or nitrogen by $R^6$ or when $X^1$ is Ser or Thr, the side chain oxygen is optionally substituted by one or more $R^1$;

$X^2$ is or L-Trp, N-methyl-D-Trp or N-methyl-L-Trp;

$X^3$ is Lys, α-N-methyl-Lys or ε-N-$(C_1-C_4)$alkyl-Lys or ε-N-[aryl-$(C_1-C_4)$alkyl]-Lys;

$X^4$ is a natural or unnatural D- or L-α-amino acid where when $X^4$ is Phe, NaI, Trp, Tyr or His, the aromatic ring thereof is optionally substituted on carbon or nitrogen by $R^8$ or when $X^4$ is Ser, Tyr or Thr, the side chain oxygen may be substituted with one or more $R^1$.

3. A compound according to claim 2, wherein each n is 2;

m is 0 or 1 to 5;

$R^1$ for each occurrence is independently H, methyl or aryl-$(C_1-C_4)$alkyl;

$R^2$ is an optionally substituted moiety selected from the group consisting phenyl-$(C_1-C_4)$alkyl and heterocyclyl-$(C_1-C_4)$alkyl, where the optionally substituted moiety is substituted by a substituent selected from the group consisting of $(C_1-C_4)$alkyl and —O—$R^6$; and $R^3$ and $R^4$ are each independently H, halo or an optionally substituted moiety selected from the group consisting of $(C_1-C_4)$alkyl and aryl; where the optionally substituted moiety is optionally substituted by a substituent selected from the group consisting of OH, $(C_1-C_4)$alkoxy, aryloxy and halo.

4. A compound according to claim 3, wherein $X^1$ is Phe, NaI, Trp, Tyr, PaI or His, wherein the aromatic ring thereof is optionally substituted on carbon or nitrogen by $R^6$; and $X^4$ is Val, Abu, Ser, Thr, NaI, Trp, Tyr or His, wherein the aromatic ring of NaI, Trp, Tyr and His is optionally substituted on carbon and/or nitrogen by $R^8$ or when $X^4$ is Ser, Tyr or Thr, the side chain oxygen is optionally substituted by $R^1$.

5. A compound according to claim 4, wherein $X^1$ is Phe, Trp or Tyr wherein the aromatic ring thereof is optionally substituted on carbon or nitrogen by $R^6$;

$X^2$ is D-Trp or N-methyl-D-Trp;

$X^3$ is Lys or α-N-methyl-Lys;

$X^4$ is Val, Thr, Abu, NaI or Tyr, wherein the side chain oxygen of the hydroxy group of Thr and Tyr is optionally substituted by $R^1$;

$R^1$ for each occurrence is independently H, methyl or benzyl;

$R^2$ is an optionally substituted moiety selected from the group consisting phenylmethyl and heterocyclylmethyl, where the optionally substituted moiety is substituted by a substituent selected from the group consisting of $(C_1-C_4)$alkyl and —O—$R^6$;

$R^3$ is $(C_1-C_4)$alkyl or optionally substituted aryl; where the optionally substituted aryl is substituted by a substituent selected from the group consisting of OH, $(C_1-C_4)$alkoxy, aryloxy, and halo;

$R^4$ is H; and $R^6$ for each occurrence is independently selected from the group consisting of H and aryl-$(C_1-C_4)$alkoxy.

6. A compound according to claim 5, wherein $X^1$ is Phe, Trp, Tyr or Tyr(OBzl);

$X^4$ is Val, Thr, Abu, NaI, or Tyr, wherein th hydroxy group of Thr and Tyr is optionally substituted benzyl;

m is 0, 2 or 4;

$R^2$ is an optionally substituted moiety selected from the group consisting of phenylmethyl and 3-indolylmethyl where the optionally substituted moiety is optionally substituted by —O—$R^6$; and $R^3$ is 1,1-dimethylethyl or optionally substituted aryl; where the optionally substituted aryl is optionally substituted by a moiety selected from the group consisting of OH, $(C_1-C_4)$alkoxy and halo.

7. A compound according to claim 6, wherein $R^2$ is phenylmethyl;

$R^3$ is 1,1-dimethylethyl or optionally substituted phenyl, where the optionally substituted phenyl is optionally substituted by OH or $OCH_3$; and $R^6$ for each occurrence is independently selected from the group consisting of H and benzylmethoxy.

8. A compound according to claim 1, wherein said compound is H-Trp-D-Trp-Lys-Abu-Phe-Ψ(4-(3-methoxyphenyl)imidazole)-Gly-OH.

9. A compound according to claim 7, wherein said compound is cyclo[Tyr-D-Trp-Lys-Val-PheΨ(4-(3-methoxyphenyl)imidazole)-Gly], cyclo[Tyr(OBzl)-D-Trp-Lys-Val-PheΨ(4-(3-methoxyphenyl)imidazole)-Gly], cyclo[Trp-D-Trp-Lys-Val-PheΨ(4-(3-methoxyphenyl)imidazole)-Gly], cyclo[Trp-D-Trp-Lys-Val-PheΨ(4-(3-hydroxyphenyl)imidazole)-Gly], cyclo[Trp-D-Trp-Lys-Thr(OBzl)-PheΨ(4-(3-methoxyphenyl)imidazole)-Gly], cyclo[Trp-D-Trp-Lys-Thr-PheΨ(4-(3-hydroxyphenyl)imidazole)-Gly], cyclo[Trp-D-Trp-Lys-Abu-PheΨ(4-(3-methoxyphenyl)imidazole)-Gly], cyclo[Phe-D-Trp-Lys-Tyr(OBzl)-PheΨ(4-(1,1-dimethylethyl)imidazole)-Gly], cyclo[Phe-D-Trp-Lys-Val-PheΨ(4-(3-methoxyphenyl)imidazole)-Gly], cyclo[Phe-D-Trp-Lys-Tyr(OBzl)-PheΨ(4-(3-methoxyphenyl)imidazole)-Gly], cyclo[Phe-D-Trp-Lys-Tyr-PheΨ(4-(3-methoxyphenyl)imidazole)-Gly],
cyclo[Phe-D-Trp-Lys-Tyr-PheΨ(4-(3-hydroxyphenyl)imidazole)-Gly],
cyclo[Trp-D-Trp-Lys-Tyr(Bzl)-PheΨ(4-(3-methoxyphenyl)imidazole)-Gly],
cyclo[Tyr-D-Trp-Lys-Val-PheΨ(4-(3-hydroxyphenyl)imidazole)-Gly],
cyclo[Phe-D-Trp-Lys-NaI-PheΨ(4-(3-hydroxyphenyl)imidazole)-Gly],
cyclo[Phe-D-Trp-Lys-NaI-PheΨ(4-(3-methoxyphenyl)imidazole)-Gly],
cyclo[Trp-D-Trp-Lys-Tyr(OBzl)-PheΨ(4-(3-methoxyphenyl)imidazole)-(γ)Abu],
cyclo[Trp-D-Trp-Lys-Tyr(OBzl)-PheΨ(4-(4-methoxyphenyl)imidazole)-Gly],
cyclo[Trp-D-Trp-Lys-Tyr(OBzl)- PheΨ(4-(phenyl)imidazole)-Gly],
cyclo[Trp-D-Trp-Lys-Tyr(OBzl)-PheΨ(4-(3-methoxyphenyl)imidazole)-(ε)Ahx] or
cyclo[Trp-D-Trp-Lys-Tyr(OBzl)-PheΨ(4-(3-hydroxyphenyl)imidazole)-(γ)Abu].

10. A compound according to claim 9, wherein said compound is
cyclo[Tyr-D-Trp-Lys-Val-PheΨ(4-(3-methoxyphenyl)imidazole)-Gly],
cyclo[Tyr(OBzl)-D-Trp-Lys-Val-PheΨ(4-(3-methoxyphenyl)imidazole)-Gly],
cyclo[Trp-D-Trp-Lys-Val-PheΨ(4-(3-methoxyphenyl)imidazole)-Gly],
cyclo[Trp-D-Trp-Lys-Val-PheΨ(4-(3-hydroxyphenyl)imidazole)-Gly],
cyclo[Trp-D-Trp-Lys-Thr(OBzl)-PheΨ(4-(3-methoxyphenyl)imidazole)-Gly],
cyclo[Trp-D-Trp-Lys-Thr-PheΨ(4-(3-hydroxyphenyl)imidazole)-Gly],
cyclo[Trp-D-Trp-Lys-Abu-PheΨ(4-(3-methoxyphenyl)imidazole)-Gly],
cyclo[Phe-D-Trp-Lys-Tyr(OBzl)-PheΨ(4-(1,1-dimethylethyl)imidazole)-Gly],
cyclo[Phe-D-Trp-Lys-Val-PheΨ(4-(3-methoxyphenyl)imidazole)-Gly],
cyclo[Phe-D-Trp-Lys-Tyr-PheΨ(4-(3-hydroxyphenyl)imidazole)-Gly] or
cyclo[Tyr-D-Trp-Lys-Val-PheΨ(4-(3-hydroxyphenyl)imidazole)-Gly].

11. A compound according to claim 10 wherein said compound is
cyclo[Tyr-D-Trp-Lys-Val-PheΨ(4-(3-methoxyphenyl)imidazole)-Gly],
cyclo[Trp-D-Trp-Lys-Val-PheΨ(4-(3-methoxyphenyl)imidazole)-Gly],
cyclo[Trp-D-Trp-Lys-Val-PheΨ(4-(3-hydroxyphenyl)imidazole)-Gly],
cyclo[Trp-D-Trp-Lys-Thr-PheΨ(4-(3-hydroxyphenyl)imidazole)-Gly],
cyclo[Trp-D-Trp-Lys-Abu-PheΨ(4-(3-methoxyphenyl)imidazole)-Gly],
cyclo[Phe-D-Trp-Lys-Val-PheΨ(4-(3-methoxyphenyl)imidazole)-Gly] or
cyclo[Tyr-D-Trp-Lys-Val-PheΨ(4-(3-hydroxyphenyl)imidazole)-Gly].

12. A compound according to claim 11 wherein said compound is
cyclo[Tyr-D-Trp-Lys-Val-PheΨ(4-(3-methoxyphenyl)imidazole)-Gly],
cyclo[Trp-D-Trp-Lys-Val-PheΨ(4-(3-hydroxyphenyl)imidazole)-Gly],
cyclo[Trp-D-Trp-Lys-Thr-PheΨ(4-(3-hydroxyphenyl)imidazole)-Gly] or
cyclo[Tyr-D-Trp-Lys-Val-PheΨ(4-(3-hydroxyphenyl)imidazole)-Gly].

13. A compound according to claim 9 wherein said compound is
cyclo[Tyr-D-Trp-Lys-Val-PheΨ(4-(3-methoxyphenyl)imidazole)-Gly],
cyclo[Trp-D-Trp-Lys-Val-PheΨ(4-(3-methoxyphenyl)imidazole)-Gly],
cyclo[Trp-D-Trp-Lys-Val-PheΨ(4-(3-hydroxyphenyl)imidazole)-Gly],
cyclo[Trp-D-Trp-Lys-Thr(OBzl)-PheΨ(4-(3-methoxyphenyl)imidazole)-Gly],
cyclo[Trp-D-Trp-Lys-Thr-PheΨ(4-(3-hydroxyphenyl)imidazole)-Gly],
cyclo[Trp-D-Trp-Lys-Abu-PheΨ(4-(3-methoxyphenyl)imidazole)-Gly],
cyclo[Phe-D-Trp-Lys-Tyr(OBzl)-PheΨ(4-(1,1-dimethylethyl)imidazole)-Gly],
cyclo[Phe-D-Trp-Lys-Tyr(OBzl)-PheΨ(4-(3-methoxyphenyl)imidazole)-Gly],
cyclo[Phe-D-Trp-Lys-Tyr-PheΨ(4-(3-hydroxyphenyl)imidazole)-Gly],
cyclo[Trp-D-Trp-Lys-Tyr(OBzl)-PheΨ(4-(3-methoxyphenyl)imidazole)-Gly],
cyclo[Tyr-D-Trp-Lys-Val-PheΨ(4-(3-hydroxyphenyl)imidazole)-Gly],
cyclo[Phe-D-Trp-Lys-NaI-PheΨ(4-(3-hydroxyphenyl)imidazole)-Gly],
cyclo[Phe-D-Trp-Lys-NaI-PheΨ(4-(3-methoxyphenyl)imidazole)-Gly],
cyclo[Trp-D-Trp-Lys-Tyr(OBzl)-PheΨ(4-(3-methoxyphenyl)imidazole)-(γ)Abu],
cyclo[Trp-D-Trp-Lys-Tyr(OBzl)-PheΨ(4-(4-methoxyphenyl)imidazole)-Gly],
cyclo[Trp-D-Trp-Lys-Tyr(OBzl)-PheΨ(4-(phenyl)imidazole)-Gly],
cyclo[Trp-D-Trp-Lys-Tyr(OBzl)-PheΨ(4-(3-methoxyphenyl)imidazole)-(ε)Ahx] or
cyclo[Trp-D-Trp-Lys-Tyr(OBzl)-PheΨ(4-(3-hydroxyphenyl)imidazole)-(γ)Abu].

14. A compound according to claim 13 wherein said compound is
cyclo[Trp-D-Trp-Lys-Thr-PheΨ(4-(3-hydroxyphenyl)imidazole)-Gly],
cyclo[Trp-D-Trp-Lys-Try(OBzl)-PheΨ(4-(3-methoxyphenyl)imidazole)-Gly],
cyclo[Phe-D-Trp-Lys-NaI-PheΨ(4-(3-hydroxyphenyl)imidazole)-Gly],
cyclo[Trp-D-Trp-Lys-Tyr(OBzl)-PheΨ(4-(3-methoxyphenyl)imidazole)-(γ)Abu],
cyclo[Trp-D-Trp-Lys-Tyr(OBzl)-PheΨ(4-(4-methoxyphenyl)imidazole)-Gly] or
cyclo[Trp-D-Trp-Lys-Tyr(OBzl)-PheΨ(4-(phenyl)imidazole)-Gly].

15. A compound according to claim 14 wherein said compound is cyclo[Trp-D-Trp-Lys-Tyr(OBzl)-PheΨ(4-(3-methoxyphenyl)imidazole)-Gly], cyclo[Trp-D-Trp-Lys-Tyr(OBzl)-PheΨ(4-(3-methoxyphenyl)imidazole)-(γ)Abu], cyclo[Trp-D-Trp-Lys-Tyr(OBzl)-PheΨ(4-(4-methoxyphenyl)imidazole)-Gly] or cyclo[Trp-D-Trp-Lys-Tyr(OBzl)-PheΨ(4-(phenyl)imidazole)-Gly].

16. A pharmaceutical composition comprising an effective amount of a compound according to claim 1 or a pharmaceutically acceptable salt thereof and a pharmaceutically acceptable carrier.

17. A pharmaceutical composition comprising an effective amount of a compound according to claim 2 or a pharmaceutically acceptable salt thereof and a pharmaceutically acceptable carrier.

18. A method of eliciting a somatostatin receptor agonist effect in a mammal in need thereof, which comprises administering to said mammal an effective amount of a compound according to claim 1 or a pharmaceutically acceptable salt thereof.

19. A method of eliciting a somatostatin receptor agonist effect in a mammal in need thereof, which comprises administering to said mammal an effective amount of a compound according to claim 2 or a pharmaceutically acceptable salt thereof.

20. A method of eliciting a somatostatin receptor antagonist effect in a mammal in need thereof, which comprises administering to said mammal an effective amount of a compound according to claim 1 or a pharmaceutically acceptable salt thereof.

21. A method of eliciting a somatostatin receptor antagonist effect in a mammal in need thereof, which comprises administering to said mammal an effective amount of a compound according to claim 2 or a pharmaceutically acceptable salt thereof.

22. A method of treating prolactin secreting adenomas, restenosis, diabetes mellitus, hyperlipidemia, insulin insensitivity, Syndrome X, angiopathy, proliferative retinopathy, dawn phenomenon, Nephropathy, gastric acid secretion, peptic ulcers, enterocutaneous and pancreaticocutaneous fistula, irritable bowel syndrome, Dumping syndrome, watery diarrhea syndrome, AIDS related diarrhea, chemotherapy-induced diarrhea, acute or chronic pancreatitis, gastrointestinal hormone secreting tumors, cancer, hepatoma, angiogenesis, inflammatory disorders, arthritis, chronic allograft rejection, angioplasty, graft vessel bleeding or gastrointestinal bleeding, in a mammal in need thereof, which comprises administering to said mammal a compound according to claim 1 or a pharmaceutically acceptable salt thereof.

23. A method of treating prolactin secreting adenomas, restenosis, diabetes mellitus, hyperlipidemia, insulin insensitivity, Syndrome X, angiopathy, proliferative retinopathy, dawn phenomenon, Nephropathy, gastric acid secretion, peptic ulcers, enterocutaneous and pancreaticocutaneous fistula, irritable bowel syndrome, Dumping syndrome, watery diarrhea syndrome, AIDS related diarrhea, chemotherapy-induced diarrhea, acute or chronic pancreatitis, gastrointestinal hormone secreting tumors, cancer, hepatoma, angiogenesis, inflammatory disorders, arthritis, chronic allograft rejection, angioplasty, graft vessel bleeding or gastrointestinal bleeding, in a mammal in need thereof, which comprises administering to said mammal a compound according to claim 2 or a pharmaceutically acceptable salt thereof.

24. A method of inhibiting the proliferation of *helicobacter pylori* in a mammal in need thereof, which comprises administering to said mammal a compound according to claim 1 or a pharmaceutically acceptable salt thereof.

25. A method of inhibiting the proliferation of *helicobacter pylori* in a mammal in need thereof, which comprises administering to said mammal a compound according to claim 2 or a pharmaceutically acceptable salt thereof.

* * * * *